(12) United States Patent
Alkhatib

(10) Patent No.: US 9,554,905 B2
(45) Date of Patent: Jan. 31, 2017

(54) APPARATUS AND METHOD FOR IMPLANTING COLLAPSIBLE/EXPANDABLE PROSTHETIC HEART VALVES

(71) Applicant: St. Jude Medical, Inc., St. Paul, MN (US)

(72) Inventor: Yousef F. Alkhatib, Edina, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 200 days.

(21) Appl. No.: 14/311,957

(22) Filed: Jun. 23, 2014

(65) Prior Publication Data

US 2014/0303722 A1 Oct. 9, 2014

Related U.S. Application Data

(63) Continuation of application No. 13/954,202, filed on Jul. 30, 2013, now Pat. No. 8,795,355, which is a
(Continued)

(51) Int. Cl.
*A61F 2/24* (2006.01)
*A61F 2/01* (2006.01)
*A61F 2/95* (2013.01)

(52) U.S. Cl.
CPC .............. *A61F 2/2436* (2013.01); *A61F 2/013* (2013.01); *A61F 2/24* (2013.01); *A61F 2/2439* (2013.01);
(Continued)

(58) Field of Classification Search
CPC ...... A61F 2/013; A61F 2/2436; A61F 2/2439; A61F 2/24; A61F 2/2418; A61F 2002/016; A61F 2230/0071; A61F 2230/0093;A61F 2002/9517; A61F 2002/018; A61F 2230/008; A61F 2/962; A61F 2/966
See application file for complete search history.

(56) References Cited

U.S. PATENT DOCUMENTS

| 3,657,744 A | 4/1972 | Ersek |
| 4,423,730 A | 1/1984 | Gabbay |

(Continued)

FOREIGN PATENT DOCUMENTS

| EP | 1129744 A1 | 9/2001 |
| EP | 1157673 A2 | 11/2001 |

(Continued)

OTHER PUBLICATIONS

Extended European Search Report for Application No. EP 11186318 dated Jul. 17, 2012.
(Continued)

*Primary Examiner* — Gregory Anderson
*Assistant Examiner* — Son Dang
(74) *Attorney, Agent, or Firm* — Lerner, David, Littenberg, Krumholz & Mentlik, LLP

(57) ABSTRACT

Apparatus for delivering a prosthetic heart valve into a patient by means that are less invasive than conventional open-chest, open-heart surgery. The prosthetic valve may be collapsed while in a delivery device. When the valve reaches the desired implant site in the patient, the valve can be released from the delivery device, which allows the valve to re-expand to the configuration in which it can function as a heart valve. For example, the delivery device may be constructed to facilitate delivery of the prosthetic valve into the patient via the apex of the patient's heart.

9 Claims, 20 Drawing Sheets

Related U.S. Application Data continuation of application No. 12/452,128, filed as application No. PCT/US2008/008022 on Jun. 26, 2008, now Pat. No. 8,512,398.

(60) Provisional application No. 60/937,361, filed on Jun. 26, 2007.

(52) U.S. Cl.
CPC ........ *A61F 2/2418* (2013.01); *A61F 2002/016* (2013.01); *A61F 2002/018* (2013.01); *A61F 2002/9517* (2013.01); *A61F 2230/008* (2013.01); *A61F 2230/0071* (2013.01); *A61F 2230/0093* (2013.01)

(56) References Cited

U.S. PATENT DOCUMENTS

| | | | |
|---|---|---|---|
| 4,723,549 | A | 2/1988 | Wholey et al. |
| 5,201,757 | A | 4/1993 | Heyn et al. |
| 5,290,249 | A | 3/1994 | Foster et al. |
| 5,324,304 | A | 6/1994 | Rasmussen |
| 5,476,510 | A | 12/1995 | Eberhardt et al. |
| 5,690,644 | A | 11/1997 | Yurek et al. |
| 5,843,167 | A | 12/1998 | Dwyer et al. |
| 5,924,424 | A | 7/1999 | Stevens et al. |
| 5,957,974 | A | 9/1999 | Thompson et al. |
| 5,968,068 | A | 10/1999 | Dehdashtian et al. |
| 5,976,172 | A | 11/1999 | Homsma et al. |
| 6,077,297 | A | 6/2000 | Robinson et al. |
| 6,139,572 | A | 10/2000 | Campbell et al. |
| 6,306,141 | B1 | 10/2001 | Jervis |
| 6,380,457 | B1 | 4/2002 | Yurek et al. |
| 6,401,720 | B1 | 6/2002 | Stevens et al. |
| 6,425,916 | B1 | 7/2002 | Garrison et al. |
| 6,623,518 | B2 | 9/2003 | Thompson et al. |
| 6,699,274 | B2 | 3/2004 | Stinson |
| 6,814,746 | B2 | 11/2004 | Thompson et al. |
| 6,830,584 | B1 | 12/2004 | Seguin |
| 7,018,406 | B2 | 3/2006 | Seguin et al. |
| 7,127,789 | B2 | 10/2006 | Stinson |
| 7,311,730 | B2 | 12/2007 | Gabbay |
| 7,510,572 | B2 | 3/2009 | Gabbay |
| 7,632,296 | B2 | 12/2009 | Malewicz |
| 7,682,390 | B2 | 3/2010 | Seguin |
| 7,794,487 | B2 | 9/2010 | Majercak et al. |
| 7,803,185 | B2 | 9/2010 | Gabbay |
| 7,993,392 | B2 | 8/2011 | Righini et al. |
| 2002/0151970 | A1 | 10/2002 | Garrison et al. |
| 2002/0161390 | A1 | 10/2002 | Mouw |
| 2003/0050694 | A1 | 3/2003 | Yang et al. |
| 2004/0210304 | A1 | 10/2004 | Seguin et al. |
| 2005/0038502 | A1 | 2/2005 | Waysbeyn et al. |
| 2005/0060016 | A1* | 3/2005 | Wu ............... A61F 2/95 623/1.11 |
| 2005/0137689 | A1* | 6/2005 | Salahieh ........... A61F 2/2418 623/2.11 |
| 2005/0137691 | A1 | 6/2005 | Salahieh et al. |
| 2005/0137695 | A1 | 6/2005 | Salahieh et al. |
| 2005/0137697 | A1 | 6/2005 | Salahieh et al. |
| 2005/0240200 | A1 | 10/2005 | Bergheim |
| 2006/0074484 | A1 | 4/2006 | Huber |
| 2006/0106415 | A1 | 5/2006 | Gabbay |
| 2006/0129235 | A1 | 6/2006 | Seguin et al. |
| 2006/0142848 | A1 | 6/2006 | Gabbay |
| 2006/0167468 | A1 | 7/2006 | Gabbay |
| 2006/0212107 | A1 | 9/2006 | Case et al. |
| 2006/0259120 | A1 | 11/2006 | Vongphakdy et al. |
| 2007/0010876 | A1 | 1/2007 | Salahieh et al. |
| 2007/0027534 | A1 | 2/2007 | Bergheim et al. |
| 2007/0043435 | A1 | 2/2007 | Seguin et al. |
| 2007/0055358 | A1 | 3/2007 | Krolik et al. |
| 2007/0073389 | A1* | 3/2007 | Bolduc ............ A61B 17/064 623/1.36 |
| 2007/0073391 | A1 | 3/2007 | Bourang et al. |
| 2007/0088431 | A1 | 4/2007 | Bourang et al. |
| 2007/0112422 | A1 | 5/2007 | Dehdashtian |
| 2007/0162100 | A1 | 7/2007 | Gabbay |
| 2007/0168013 | A1 | 7/2007 | Douglas |
| 2007/0203575 | A1 | 8/2007 | Forster et al. |
| 2007/0239271 | A1 | 10/2007 | Nguyen |
| 2007/0244552 | A1 | 10/2007 | Salahieh et al. |
| 2007/0254273 | A1 | 11/2007 | LaFrance et al. |
| 2007/0269784 | A1 | 11/2007 | LaFrance et al. |
| 2007/0270932 | A1* | 11/2007 | Headley ............ A61F 2/95 623/1.11 |
| 2008/0071369 | A1 | 3/2008 | Tuval et al. |
| 2008/0147182 | A1 | 6/2008 | Righini et al. |
| 2009/0054975 | A1 | 2/2009 | del Nido et al. |
| 2010/0004740 | A1 | 1/2010 | Seguin et al. |
| 2010/0286768 | A1 | 11/2010 | Alkhatib |
| 2010/0298931 | A1 | 11/2010 | Quadri et al. |
| 2011/0224678 | A1 | 9/2011 | Gabbay |

FOREIGN PATENT DOCUMENTS

| | | |
|---|---|---|
| WO | 2006/076890 A1 | 7/2006 |
| WO | 2007071436 A2 | 6/2007 |
| WO | 2008070797 A2 | 6/2008 |
| WO | 2008/097590 A1 | 8/2008 |
| WO | 2010051025 A1 | 5/2010 |
| WO | 2010087975 A1 | 8/2010 |

OTHER PUBLICATIONS

PCT International Search Report date Oct. 10, 2008.
Ruiz, Carlos, Overview of PRE-CE Mark Transcatheter Aortic Valve Technologies, Euro PCR (powerpoint—dated May 25, 2010).

\* cited by examiner

APPARATUS AND METHOD FOR IMPLANTING COLLAPSIBLE/EXPANDABLE PROSTHETIC HEART VALVES

This application is a continuation of U.S. patent application Ser. No. 13/954,202, filed Jul. 30, 2013, which is a continuation of U.S. patent application Ser. No. 12/452,128, filed Dec. 16, 2009, U.S. Pat. No. 8,512,398, which is a national phase entry under 35 U.S.C. §371 of International Application No. PCT/US2008/008022, filed Jun. 26, 2008, published in English, which claims the benefit of the filing date of U.S. provisional patent application 60/937,361, filed Jun. 26, 2007, the disclosures of which are hereby incorporated by reference herein in their entirety.

BACKGROUND OF THE INVENTION

This invention relates to collapsible/expandable prosthetic heart valve delivery systems which can house, retain, maintain, transport, deploy, help anchor, and release (and, if necessary, reposition and/or retrieve) a collapsible prosthetic heart valve via a minimally invasive (or at least reduced invasiveness) port access, e.g., at the apex of a patient's heart and through the intercostal space of the patient's ribs.

The field of collapsible/expandable prosthetic heart valves is relatively new. The general idea is to provide a prosthetic heart valve that can be collapsed to a relatively small size (diameter) for delivery into the patient with reduced invasiveness to the patient's body (typically via a tube of relatively small diameter). When the valve reaches the desired implant site in the patient, the valve is released from the delivery apparatus and expanded to its full operating size. This also includes securing the valve to tissue of the patient at the implant site.

There are several approaches to delivering and deploying such collapsible/expandable prosthetic heart valves using arterial or venous systems of the patient. However, these approaches may impose certain constraints, such as requiring smaller delivery system profiles (cross sections) so that they can be used in diseased and smaller vessels and to minimize emboli risk. This may result in undesirable trade-offs in valve design and performance in order to accommodate the demand for delivery of the valve through smaller delivery system profiles.

Ideally, the delivery system should be designed around a durable and efficient valve design, thus not compromising any of the valve's long-term implant performance requirements. In doing so, the valve design should be adequate for its intended performance and long-term durability functions. This may result in valve profiles in the collapsed state that are somewhat larger than would be appropriate for human artery or vein delivery approaches, thereby calling for an alternative route to delivering the valve to its intended implant site.

The transseptal (through the septum of the heart) antegrade (delivery in the same direction as native blood flow) approach is one approach that has been tried. In the transseptal approach, access is gained through the venous circulatory system leading to the right atrium. A puncture is made through the septum wall separating the left and right atria (hence the term transseptal). The catheter is then advanced through the mitral valve into the left ventricle and looped back up ending at the aortic valve. This approach may have some disadvantages, however. For example, it may result in damage to the mitral valve and the associated chordae when trying to gain access to the aortic valve. In contrast, the transapical (through the apex of the heart) antegrade approach may offer a better and safer alternative for entering the left ventricle ("LV") for direct access to the aortic and mitral valves. (See, for example, P. Tozzi et al., "Endoscopic off-pump aortic valve replacement: does the pericardial cuff improve the sutureless closure of left ventricular access?", European Journal of Cardio-thoracic Surgery 31 (2007) 22-25, available online 6 Sep. 2006.) Accessing the LV through a small port at the apex (lower end) of the heart is not new, as this has been the practice for several decades in placing bypass shunts in pediatrics. There are good, long-term, clinical experiences with this access approach to render it safe and effective. With an optimum delivery system design, safer and more effective direct access to the aortic or mitral valve can be achieved for the purposes of repair and/or replacement of defective native valves.

SUMMARY OF THE INVENTION

The delivery system of the present invention may comprise several components working together to facilitate various functions required for delivery and deployment of a collapsible/expandable prosthetic heart valve. The delivery system may include an elongated shaft attached to an ergonomic handle. The handle may incorporate several controls for several functional features within the device. One of these controls may be a rotating wheel that functions to advance/retract the valve prior to deployment and final release. Another control may be an outer shaft, which may contain a polymer sheath that functions as the valve-collapsing/expanding mechanism. Inside the outer shaft and within the sheath, there may be an internal movable shaft that is connected to the delivery device tip at the distal end of the delivery system. The shaft may be notched such that a wheel with teeth can engage and move the shaft axially when rotated in either direction (advance or retract). The prosthetic heart valve may be mounted onto this shaft and between the tip and a base. The base platform may function as a valve holding and constraining mechanism. The valve may rest on this base and can be secured in place using various mechanisms. For example, the base can have features and through-holes to allow the valve's proximal struts to be securely fastened using a suture that runs to the outside of the device at the handle on the proximal end. When the operator is satisfied with the position and orientation of the valve, the valve can be released by cutting and pulling out this suture. Alternatively, other mechanisms can be employed to secure the valve in place until final release.

The internal movable shaft may contain multi-lumens that connect manifold ports at the proximal end of the device to one or more openings at or near the distal end (tip). These lumens can be utilized for various functions such as delivery of fluids (saline, contrast, etc.) and deployment of embolic protection devices, balloons for valvuloplasty, etc.

Outside the outer shaft, a spring-loaded, donut-shaped component can be included to aid in sealing the apex of the heart or other access at the entry point by way of gentle pressure driven by the spring.

The delivery system can be manufactured from materials that are known to be biologically compatible for short-term human interaction, since this device is not a permanent implant. However, material selection should take into account the fact that this device will come into contact with a permanent implant.

The device handle can be injection molded from a biocompatible polymer material. The elongated shaft can be polymeric or laser cut/machined surgical grade stainless steel. Internal working components can be either from a polymeric origin, stainless steel, shape-memory nitinol (nickel/titanium alloy) material, etc., depending on each component's function and performance requirements. The manifold can be an injection molded polycarbonate. The sealing donut can be made from various durometers of silicone. The device components may fit together using various means of interference fit, tabs, slots, glue, polymer heat bonds, and/or locking mechanisms to facilitate a seamless working system.

Various advantageous features of the invention are identified (to some extent recapitulating the foregoing) in the next several paragraphs.

Certain aspects of the invention relate to providing an ergonomic, hand-held, easy-to-use delivery system for collapsible/expandable prosthetic heart valves. Such a delivery system may include a handle and an elongated shaft that houses the valve. The handle can incorporate controls for specific functional features within the device.

The delivery system may include valve release, retrieve, and/or reposition mechanisms.

The device may include one or more radio-opaque marker bands (e.g., at or near the distal tip) for guidance and visualization of the delivery system (especially the distal end) under fluoroscopy in the case of all-polymer construction.

The device may include precision, wheel-driven, advance/retract capabilities for precise valve positioning. Alternate mechanisms (e.g., a sliding lever) are also possible.

The device may include capabilities for fully deploying the valve but not releasing it when recapture is desired.

The device may include multi-lumen capabilities in the shaft for procedural support using ancillary devices such as guide wires, balloon catheters, embolic protection devices, fluids delivery (flushing or visualization), etc.

The valve can be secured to internal features of the delivery system using different configurations. One way is to secure the proximal end of the valve to a holder base (e.g., using sutures, mechanical interference fit features, etc.). Another way is to utilize a suture (or polymer-covered thin wire or any other appropriate means similar to this) to run from the proximal end of the device (handle) through specifically designed structures within the valve. This strand can then run through specifically designed channels in the device tip and back inside the central lumen (or other specific lumen) and end outside the device by the handle where the operator can control it. Tensioning or loosening this wire/suture will cause the valve to deploy or re-collapse. This can be used to partially deploy the valve and recapture it for repositioning or retrieval as desired.

A movable sheath, with an independent control at the handle, can function as the valve collapsing/expanding mechanism by advancing/retracting the sheath over the valve. The sheath may also maintain and protect the valve in the collapsed state. The sheath can also facilitate partial deployment and expansion of the valve, e.g., so that the operator of the apparatus can check for appropriate positioning of the valve in the patient.

The device may include features in the tip and valve holder base to control valve orientation within the delivery system so that the valve can be deployed with the correct angular orientation about its longitudinal axis, e.g., to align commissures of the prosthetic valve relative to commissures of the native valve as desired. These features can be undercuts or depressions that correspond to features on the prosthetic valve, for example.

Along with the conventional purse-string suture, a spring-loaded, silicone, molded, donut-shaped component can aid in sealing the entry port at the apex of the heart or other access into the patient's circulatory system.

The device may include the capability of opening and closing off access to any of the lumen ports at the back manifold connector.

The device tip may include features that allow the valve distal end to rest in a manner that controls the valve's collapsed diameter (e.g., to prevent damage to the stent and valve leaflets during collapse of the valve for minimally invasive delivery).

The delivery system can include a fork-like structure that can protrude and extend outside the shaft near the distal end to force open calcified native heart valve leaflets (e.g., into the sinuses of the valsalva) in preparation for valve deployment and release. Another example of an embodiment for such purposes is to deploy a structure like an umbrella. Such an umbrella design can serve two functions: (1) calcified leaflet retention, pushing such native leaflet structures out of the way in preparation for new valve deployment, and (2) embolic protection, which can be achieved by incorporating a fine mesh within the deployed ribs of the umbrella, thus capturing any emboli from the procedure. Once the procedure is completed, this umbrella can be collapsed and retracted back into the shaft, thereby safely removing from the patient all emboli and any calcified debris. An example of a structure that can be used to collapse the umbrella when desired includes a thin strand (e.g., wire or suture) attached to each of the umbrella ribs. These strands extend into the main central lumen. Pulling these strands from the proximal end causes the ribs of the umbrella to collapse.

The delivery system wheel can be centered in the handle for rotation access from both sides of the handle, or it can be offset to protrude from only one side of the device handle.

The device preferably contains seals in various areas to prevent blood from seeping through the various channels and outside the heart.

Further features of the invention, its nature and various advantages, will be more apparent from the accompanying drawings and the following detailed description.

DETAILED DESCRIPTION

Figure 1:
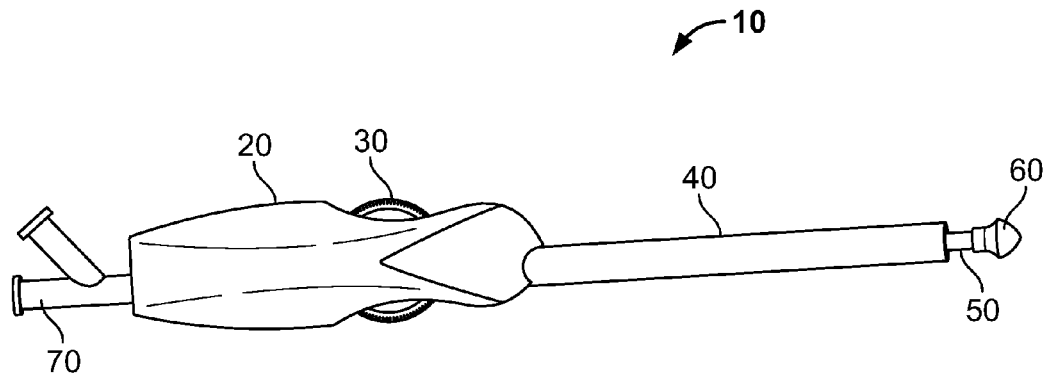
FIG. 1 is a simplified elevational view of an illustrative embodiment of apparatus in accordance with the invention.

An illustrative embodiment of prosthetic heart valve delivery apparatus 10 in accordance with the invention is shown in FIG. 1. FIG. 1 and several subsequent FIGS. omit all depiction of the prosthetic valve, but several still later FIGS. do show examples of such valves. The components of apparatus 10 that are visible in FIG. 1 include handle 20, control wheel 30, outer shaft 40, inner shaft 50, distal tip 60, and proximal (back) manifold connector 70. Elements 40 and 70 are both fixed to handle 20. Control wheel 30 is rotatable about an axis (perpendicular to the plane on which FIG. 1 is drawn) to cause shaft 50 (and distal tip 60) to advance or retract relative to shaft 40, depending on the direction of rotation of the control wheel. Distal tip 60 is fixed on the distal end of shaft 50. Connector 70 may include one or more lumens that communicate with one or more lumens through other components of the apparatus.

Elements 20, 30, and 70 remain outside the patient at all times. Elements 40, 50, and 60 are designed for insertion into a patient's body in a low invasiveness manner to deliver a prosthetic heart valve into the patient and to deploy (implant) that prosthetic heart valve in the patient. More particularly, the prosthetic heart valve is initially contained (in a collapsed condition) in a distal portion of apparatus 10 (i.e., inside shaft 40, concentrically around shaft 50, and abutting distal tip 60). In this condition of the apparatus, shaft 40 may help to keep the valve collapsed, and distal tip 60 (which is proximally retracted) may help to keep the valve inside shaft 40. When the distal portion of the apparatus reaches the desired implant site for the valve in the patient, wheel 30 can be rotated to extend distal tip 60, a distal portion of shaft 50, and the prosthetic heart valve from the distal end of shaft 40. This allows the prosthetic heart valve to expand radially outwardly from shaft 50 to its full operating size, which also causes the valve to engage surrounding native tissue of the patient and thereby implant in the patient. The apparatus can then be withdrawn (proximally) from the patient. In particular, distal tip 60 comes out through the center of the now-expanded valve.

More details regarding the foregoing will be provided later in this specification.

It should be noted that in the FIG. 1 embodiment, shaft 40 is off-center relative to handle 20 (i.e., shaft 40 is somewhat below the top-to-bottom center of handle 20). On the other hand, wheel 30 is centered on handle 20 and is exposed for operation from either above or below the handle.

Figure 2:
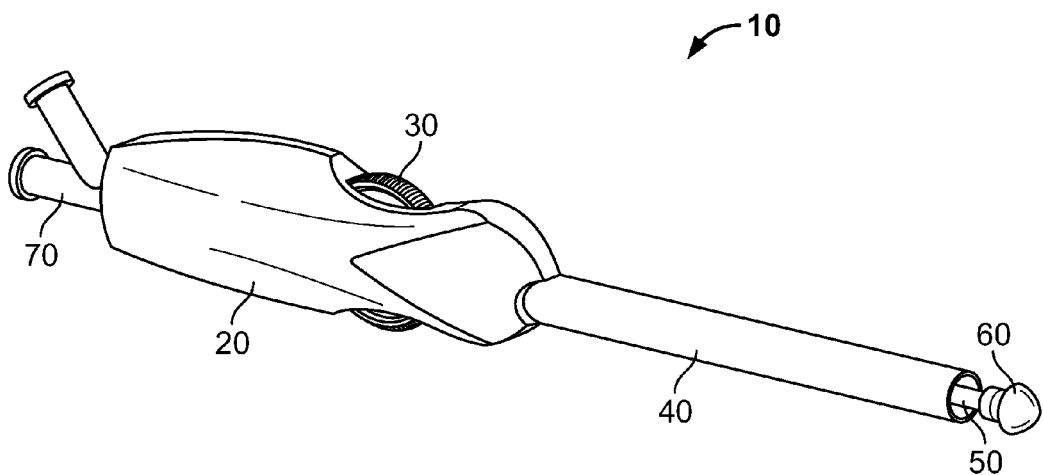
FIG. 2 is a simplified isometric or perspective view of the FIG. 1 embodiment.
Figure 3:
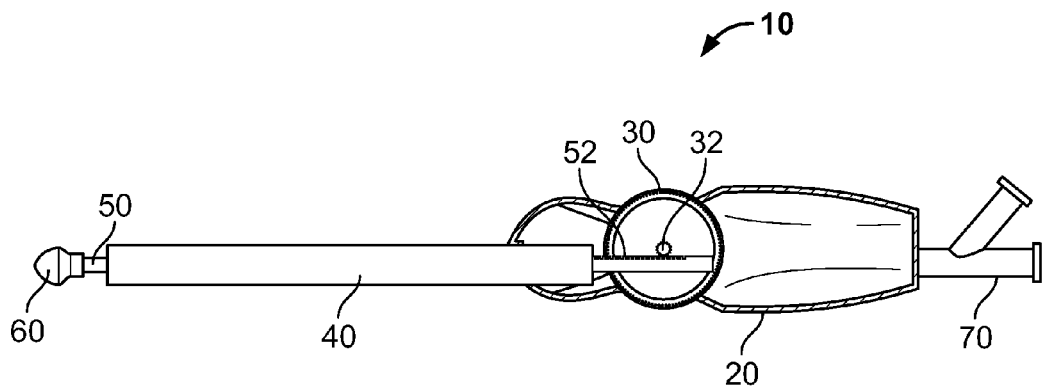
FIG. 3 is another simplified elevational view (with portions removed to reveal some of the interior) of the FIG. 1 embodiment.

FIGS. 2 and 3 show other views of apparatus 10. FIG. 3 shows apparatus 10 with half of handle 20 removed. This exposes the connection between wheel 30 and shaft 50. In particular, it shows that there is a spur gear 32 on wheel 30 concentric with the axis of rotation of wheel 30. This spur gear engages with a rack 52 on shaft 50. These features allow rotation of wheel 30 to cause translation of shaft 50 along its longitudinal axis. (Features of this kind may be seen even more clearly for another embodiment in FIG. 5.)

Figure 4:
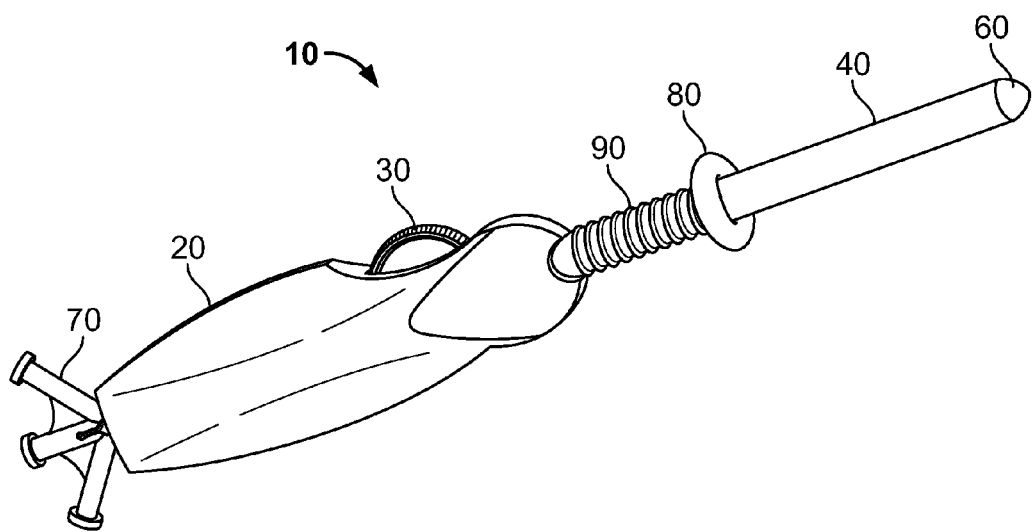
FIG. 4 is a simplified isometric or perspective view of another illustrative embodiment of apparatus in accordance with the invention.

An alternative embodiment of device 10 is shown in FIG. 4. Even though the FIG. 4 embodiment is somewhat different than the FIGS. 1-3 embodiment, the same reference numbers continue to be used for generally similar elements. Thus additional information for such elements can be gleaned from earlier description of those elements, and it will not be necessary to repeat everything previously said for elements that are used again (at least in generally similar form) in different embodiments.

The FIG. 4 embodiment is different from the FIGS. 1-3 embodiment in that in FIG. 4 shaft 40 is centered (from top to bottom) on handle 20. Another difference is that in FIG. 4, control wheel 30 is only operable from the top of handle 20.

FIG. 4 shows the possible addition of a toroidal or donut-shaped sealing ring 80 disposed concentrically around an intermediate portion of the length of shaft 40. Ring 80 fits relatively closely around the outside of shaft 40, but ring 80 is also axially slidable along shaft 40. If ring 80 is moved in the proximal direction from the approximate starting position shown in FIG. 4, coil spring 90 (also disposed concentrically around shaft 40) acts to resiliently urge it back toward the starting position. Ring 80 can be located along shaft 40 so that when the distal portion of shaft 40 is pushed through an opening (aperture) in the apex of the patient's heart or other access to the patient's circulatory system, ring 80 bears against the outer surface of the tissue around the aperture and helps to reduce blood leakage from the circulatory system via the aperture. Spring 90 keeps ring 80 resiliently pressed against the outside of the tissue for this purpose. Ring 80 may be made of a softer material than other components of apparatus 10. For example, ring 80 may be made of silicone.

Figure 5:
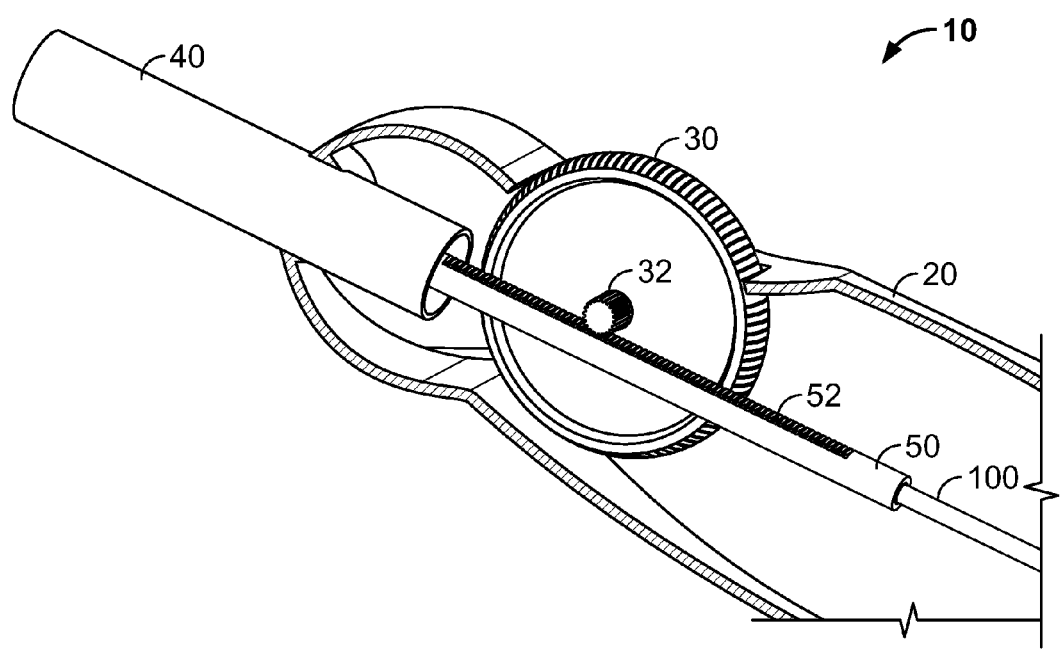
FIG. 5 is a simplified partial elevational or perspective view (with portions removed to reveal some of the interior) of the FIG. 4 embodiment.

FIG. 5 shows an enlargement of a portion of the FIG. 4 embodiment with part of handle 20 removed. Thus FIG. 5 shows the spur gear 32 on wheel 30 engaging the rack 52 on shaft 50 as described earlier in connection with FIG. 3. FIG. 5 also shows a tube 100 that may extend from connector 70 to a distal portion of the apparatus. For example, tube 100 may extend to opening 62 in the distal end of tip 60 for allowing fluid introduced via connector 70 to be released into the patient from the distal end of tip 60 for such purposes as providing fluoroscopically visible contrast in the patient. There may be more than one such tube 100, which may go to different destinations in the device, and which may be for different purposes. Note that shaft 50 may be translatable axially (i.e., lengthwise) relative to tube 100.

Figure 6:
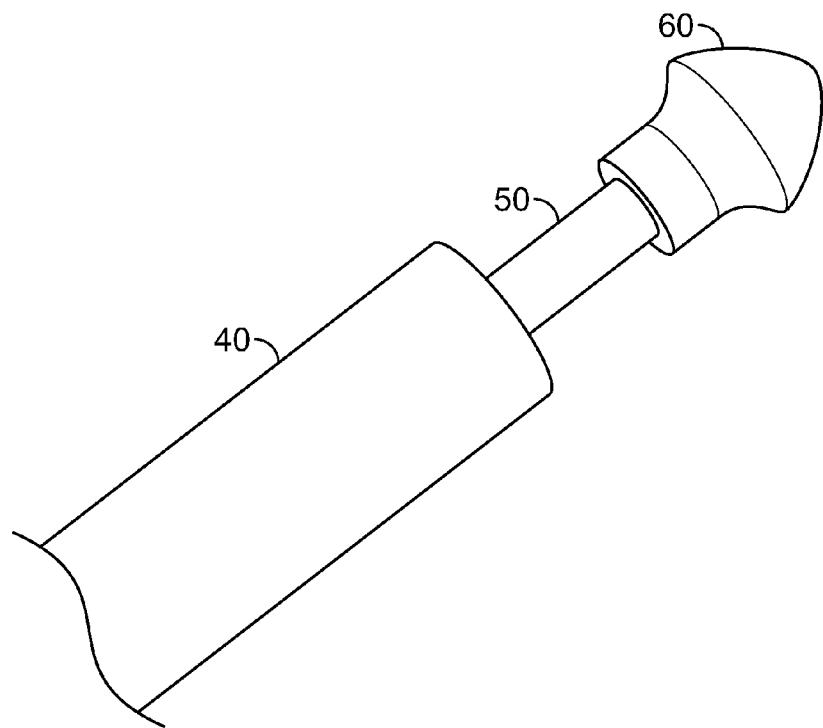
FIG. 6 is a simplified elevational or perspective view of portions of the above-mentioned embodiments.
Figure 7:
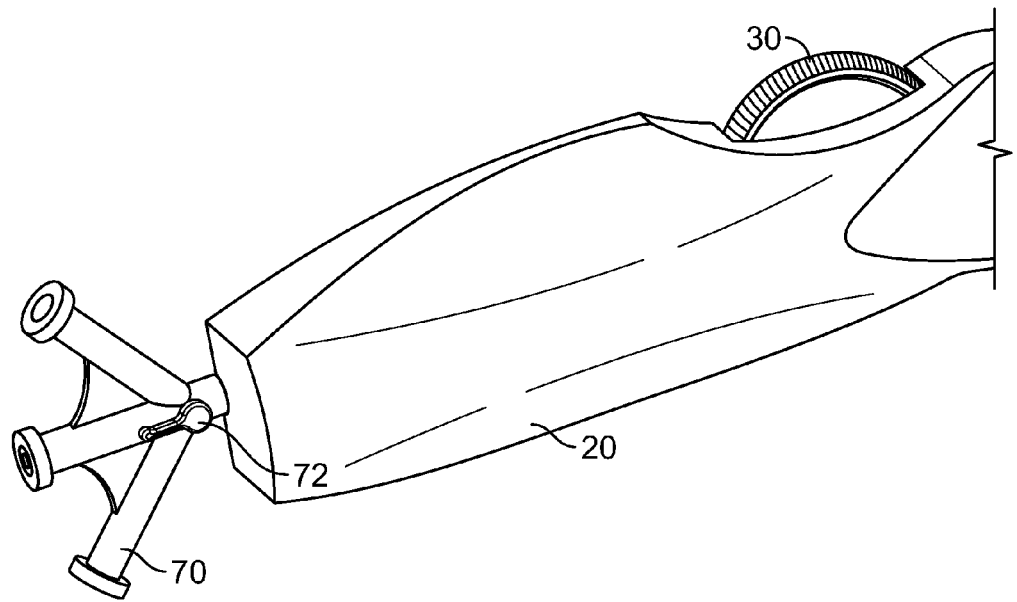
FIG. 7 is a simplified elevational or perspective view of portions of the FIG. 4 embodiment.

FIG. 6 shows portions of elements 40 and 50 and element 60 on a larger scale. FIG. 7 does the same for a portion of element 20 and element 70. FIG. 7 also shows that element 70 may include a valve 72 for selectively closing a lumen through that element. In particular, valve 72 may be controlled by the operator of the apparatus to close a lumen through connector 70, e.g., to prevent blood from escaping from the patient via that lumen. When desired, the operator may open valve 72, e.g., to allow fluid or some other auxiliary material or apparatus to be introduced into the patient via the associated lumen. Depicted valve 72 may be repeated for other lumens if desired.

Figure 8:
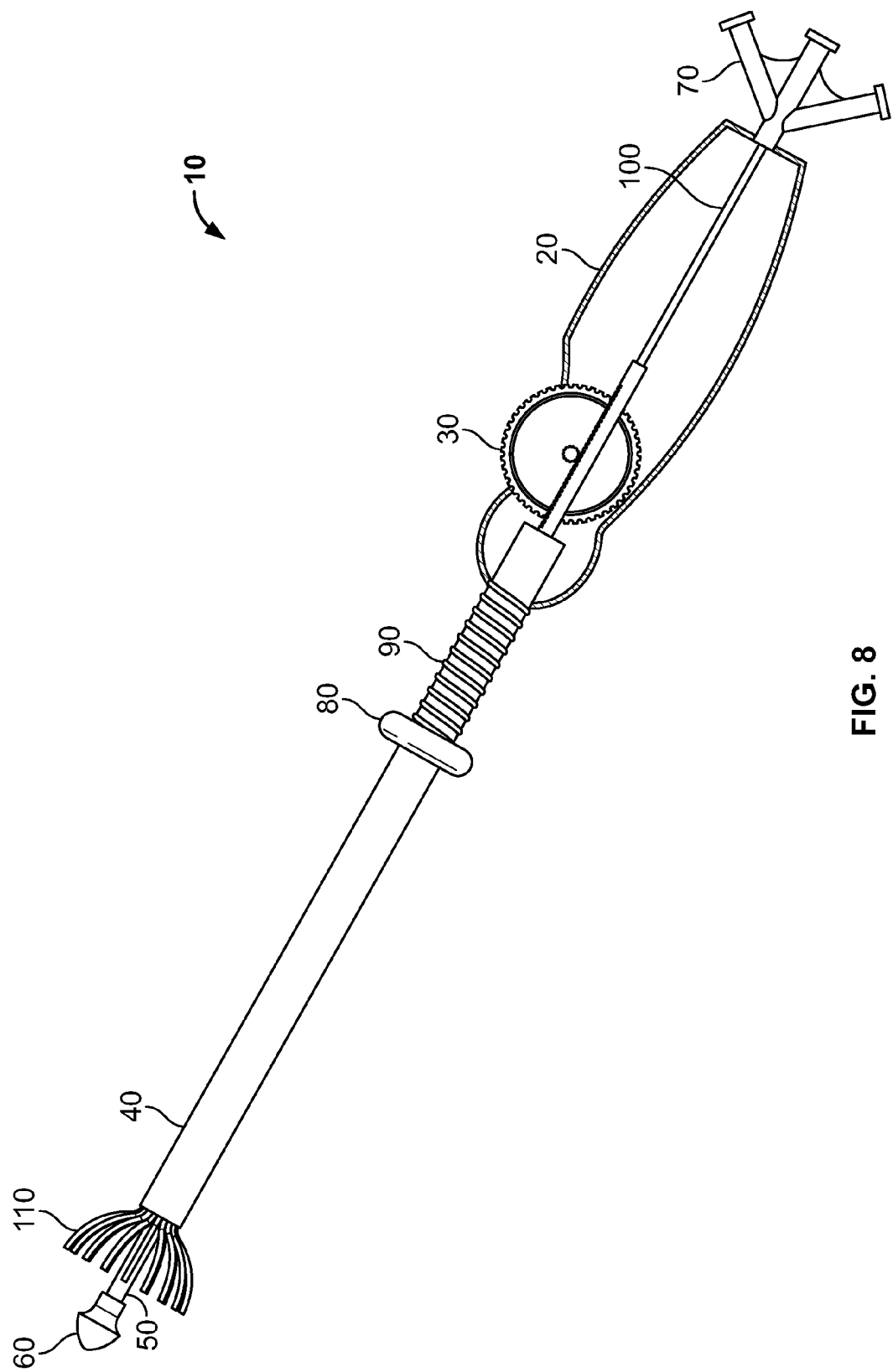
FIG. 8 is a simplified elevational view (with some portions removed) of an illustrative embodiment of apparatus that can be like the FIG. 4 embodiment, with possible additional structure in accordance with the invention.
Figure 30:
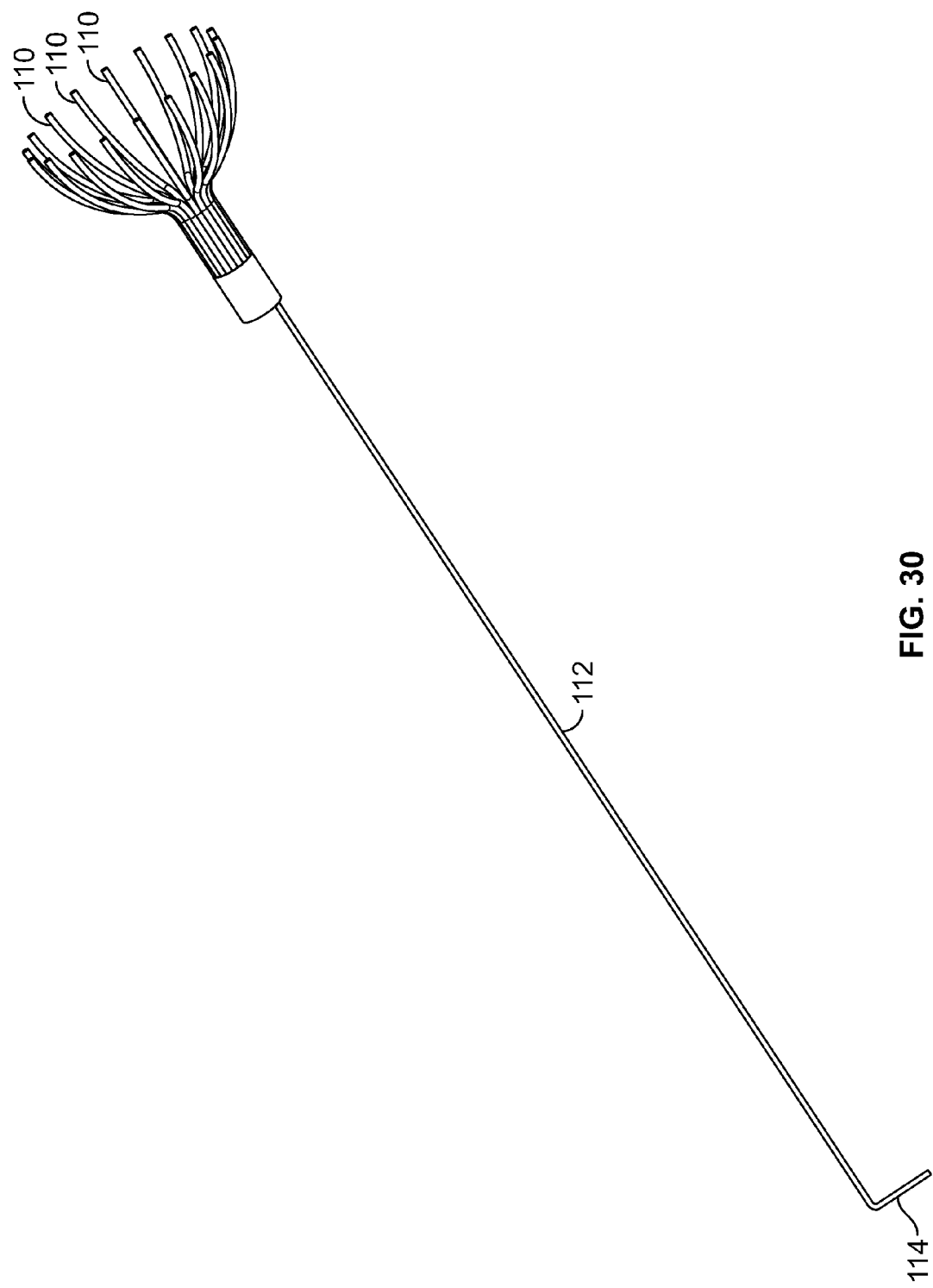
FIG. 30 is a simplified perspective or isometric view of an illustrative embodiment of a structure that can be used in apparatus in accordance with the invention.

FIG. 8 shows an illustrative embodiment of a possible addition to what has been shown before. In particular, FIG. 8 shows that a plurality of fingers 110 may be selectively deployed from the distal end of shaft 40 (when distal tip 60 is moved somewhat away from that distal shaft end) to push back native leaflets of a patient's native heart valve (which is going to be replaced by the prosthetic heart valve delivered by device 10). Fingers 110 may be initially confined in an annular array inside a distal portion of shaft 40. When it is desired to deploy them (typically when the distal portion of the apparatus is appropriately positioned relative to the native valve that is to be replaced), fingers 110 can be pushed (part way) from the distal end of shaft 40, and they then resiliently extend (radially) out farther from central shaft 50, albeit still in an annular array as shown in FIG. 8. In this condition, fingers 110 push back the leaflets of the native valve (e.g., into the patient's native valsalva sinus) in order to help make appropriate room for deployment of the prosthetic valve within the native valve. As shown in FIG. 30, fingers 110 may be attached to a shaft 112 that runs longitudinally inside shaft 40 into handle 20. Fingers 110 and their shaft 112 can be advanced or retracted relative to shaft 40 via a sliding control, lever, or the like that is on the outside of handle 20. For example, FIG. 30 shows a control member 114 attached to the proximal end of shaft 112. Control member 114 can project from a slot in a side of handle 20, where it can be manipulated by the user of the apparatus to advance or retract fingers 110. Alternatively, control member 114 may connect to another actuator element on handle 20 for the same purpose as described in the preceding sentence.

Figure 9:
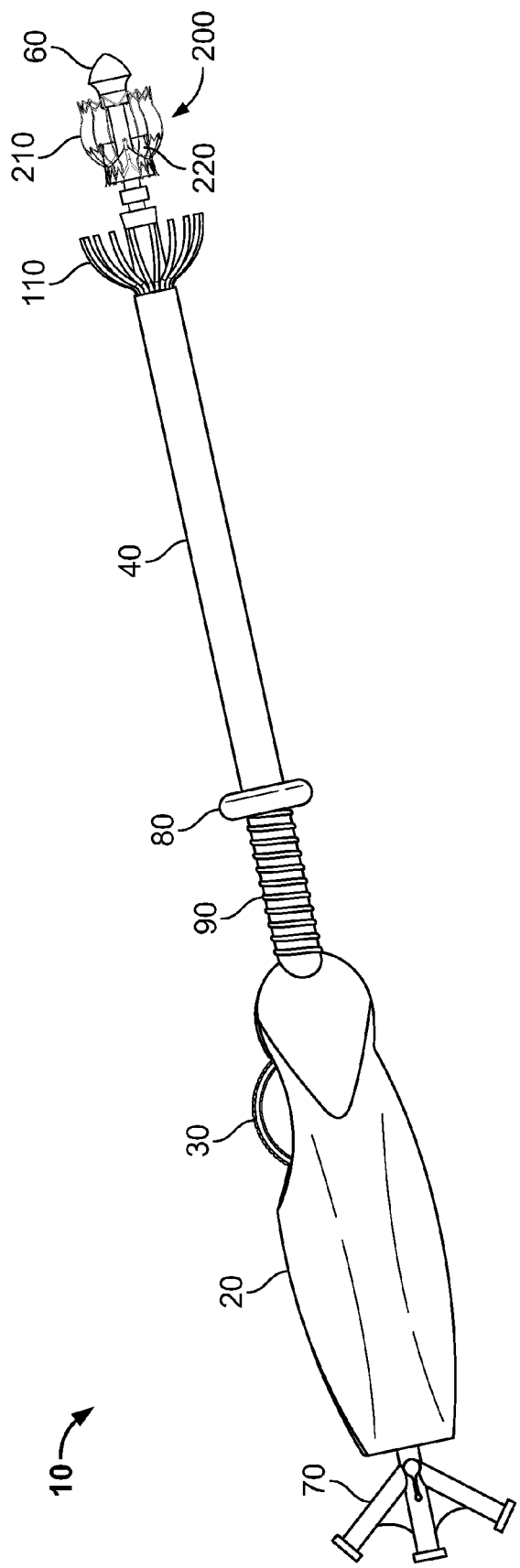
FIG. 9 is another view that is generally like FIG. 8, but for a later stage in use of the apparatus in accordance with the invention.

FIG. 9 shows a structure similar to what is shown in FIG. 8, with the addition of prosthetic valve 200 now deployed from near the distal end of the apparatus. Subsequent FIGS. show valve 200 and its deployment on a larger scale and in more detail, so more detailed discussion of the valve will be provided later in connection with those other FIGS. Here it is preliminarily noted that the principal components of valve 200 include an annular framework 210 (e.g., of metal) and a plurality of flexible valve leaflets 220 disposed within and mounted on that framework. Framework 210 and leaflets 220 are radially collapsible to a circumferential size that can fit inside shaft 40. However, when shifted beyond the distal end of shaft 40 as shown in FIG. 9, framework 210 can resiliently expand (as shown in FIG. 9), carrying leaflets 220 with the frame and positioning those leaflets relative to one another so that they can operate as a one-way, blood flow, check valve (like the native heart valve being replaced).

Figure 10:
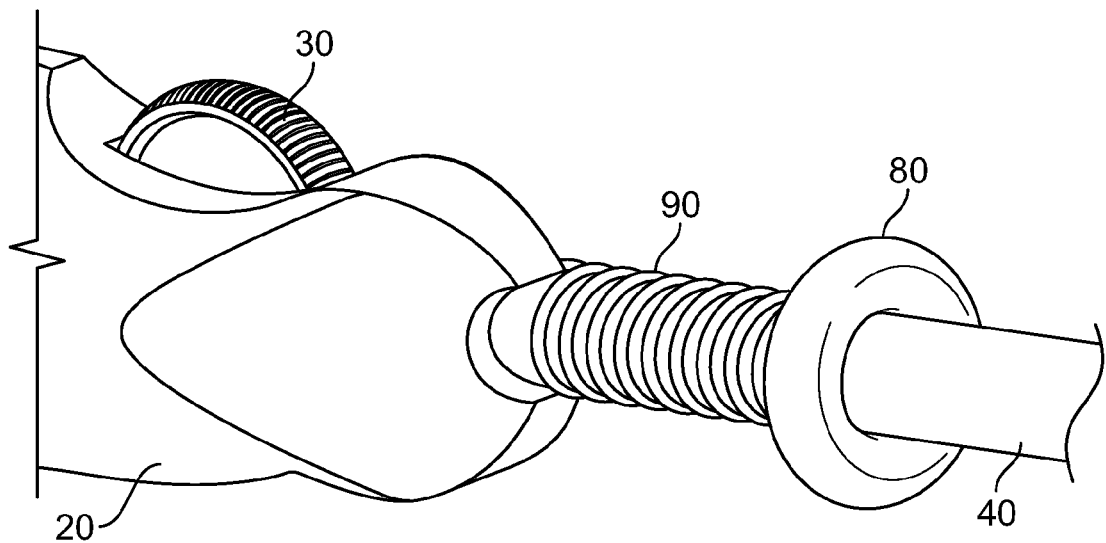
FIG. 10 is a simplified isometric or perspective view of portions of the FIG. 4 apparatus.
Figure 11:
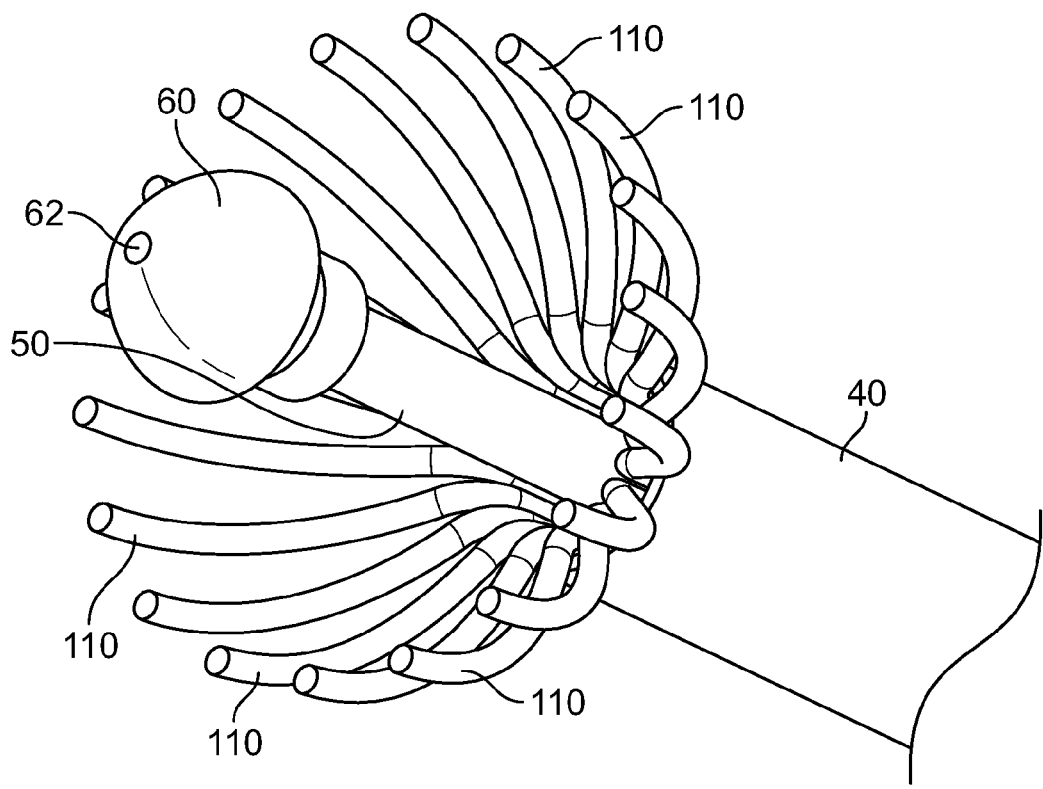
FIG. 11 is a simplified isometric or perspective view of portions of FIG. 8.

FIG. 10 shows elements 80 and 90 (and portions of neighboring elements) on a still larger scale. FIG. 11 does the same for elements 110 and portions of neighboring elements. Note the opening 62 in the distal end of tip 60, which opening may communicate with a lumen through above-described tube 100.

Figure 12:
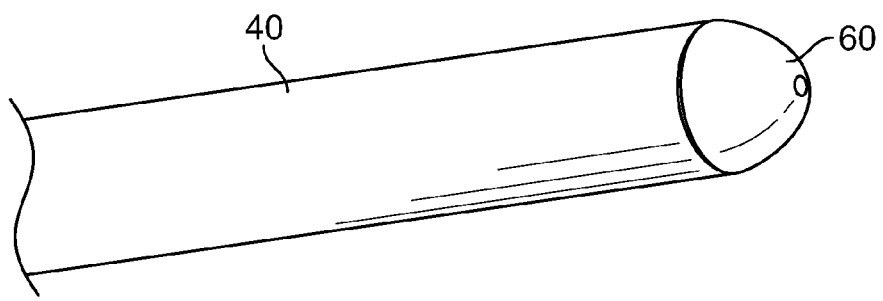
FIG. 12 is a simplified isometric or perspective view of portions of FIG. 4.

FIGS. 12-20 show an illustrative embodiment of how valve 200 may be deployed. These FIGS. focus on valve 200 and the distal portion of delivery apparatus 10. FIG. 12 shows this portion of the apparatus in the condition that it has as it is being introduced into the patient (e.g., via an aperture in the apex of the patient's heart). Note that tip 60 is against the distal end of shaft 40 to give this portion of the apparatus a smooth exterior surface.

Figure 13:
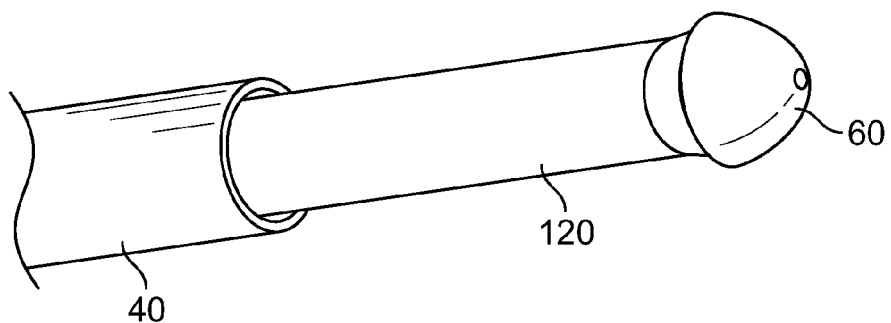
FIG. 13 is a view similar to FIG. 12 for a later stage of operation of the apparatus in accordance with the invention.

When the distal portion of apparatus 10 reaches the desired location in the patient (i.e., the desired location for implanting the prosthetic heart valve), distal tip 60 and some associated structure may be displaced distally from the distal end of shaft 40 as shown in FIG. 13. This may be done by rotating wheel 30. In addition to what has been shown in earlier FIGS., FIG. 13 shows that the apparatus may include a sleeve 120 around the outside of collapsed valve 200, but inside collapsed fingers 110. This sleeve may help to protect valve 200 from fingers 110, and it may also facilitate the staged deployment of valve 200. As FIG. 13 shows, sleeve 120 initially moves in the distal direction with tip 60 and other elements that are inside sleeve 120.

Figure 14:
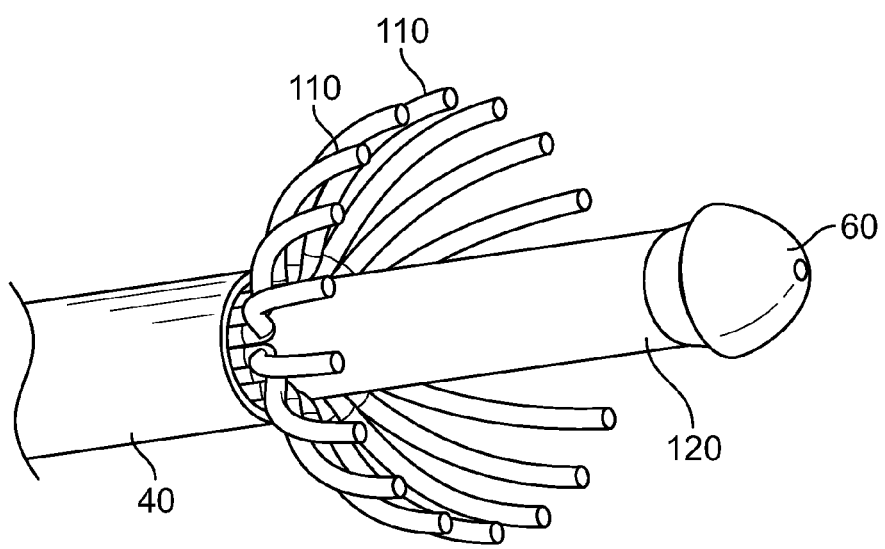
FIG. 14 is another view similar to FIG. 13 for a still later stage in operation of the apparatus in accordance with the invention.

The next step is shown in FIG. 14. In this step, fingers 110 are pushed part way out of the distal end of shaft 40 so that these distal portions of fingers 110 can spread radially outwardly and thereby push back the leaflets of the patient's native heart valve. A point should be made here as follows. FIG. 14 and subsequent FIGS. may show the apparatus that is inside deployed fingers 110 at locations that are more distal to fingers 110 than would actually be the case. For example, elements 120 and 60 may not be distally as far from fingers 110 after deployment of those fingers as is shown in FIG. 14 (and subsequent FIGS.). Instead, valve 200 may be deployed closer to deployed fingers 110 than the FIGS. alone may suggest. The FIGS. deviate from what may be the actual practice in this respect so that various parts can be seen more clearly (i.e., without overlapping and thereby obscuring one another).

Figure 15:
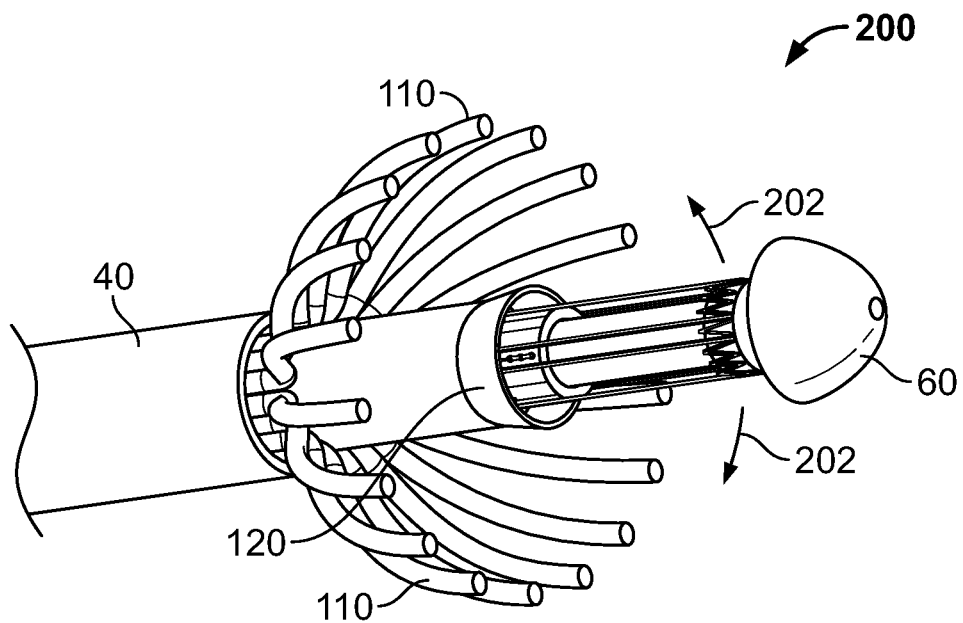
FIG. 15 is still another view similar to FIG. 14 for an even later stage in operation of the apparatus in accordance with the invention.
Figure 29:
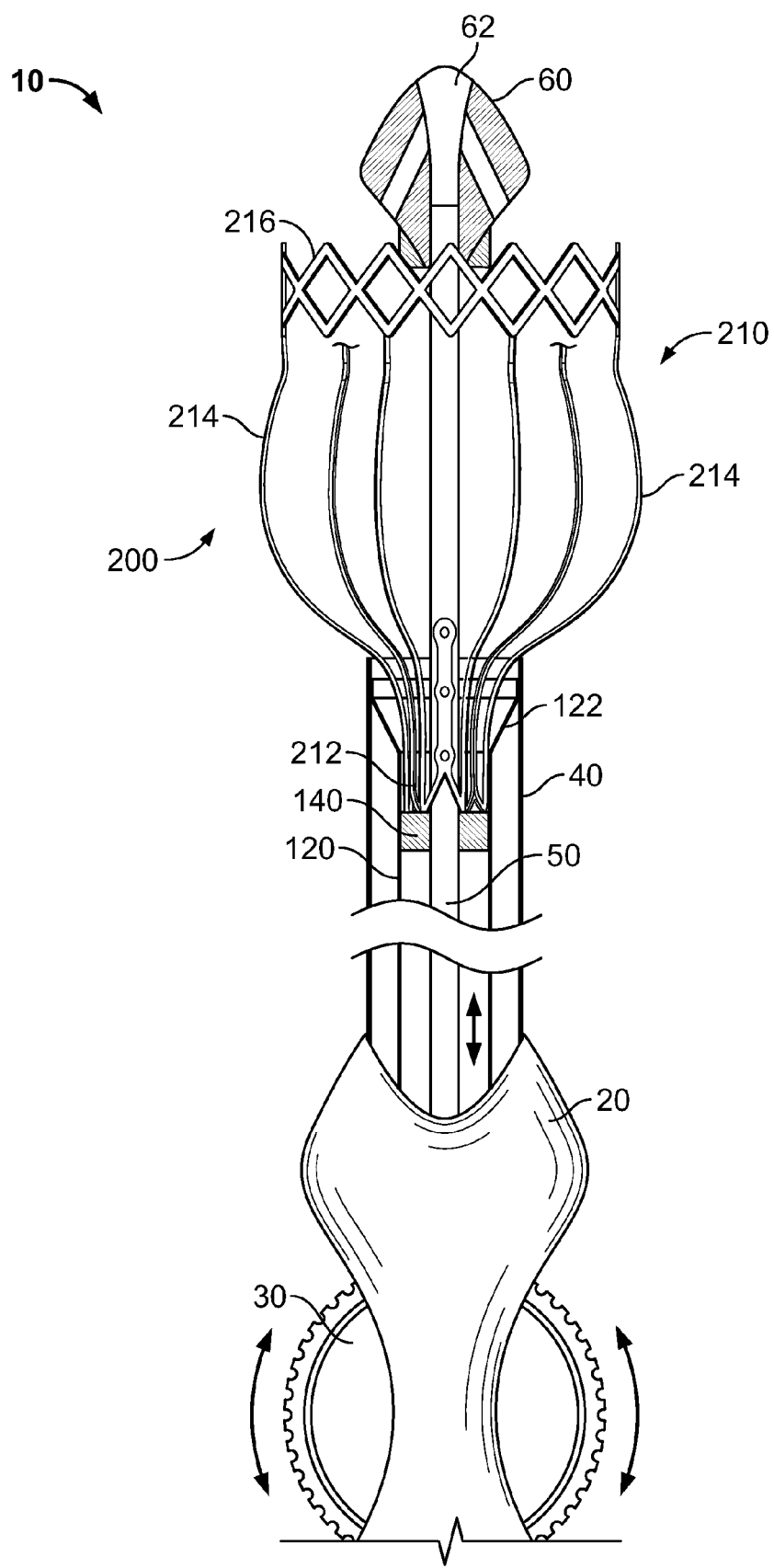
FIG. 29 is a simplified, partial, elevational view, partly in section, showing an illustrative embodiment of still other possible features in accordance with the invention.

The next step is illustrated by FIG. 15. In this step, sleeve 120 is pulled back proximally to begin to expose prosthetic heart valve 200. Although not shown in full detail in FIG. 15 to avoid over-complicating the drawing, the distal portion of heart valve 200 typically begins to deploy (i.e., expand radially outwardly as indicated by arrows 202) as it is released from confinement within sleeve 120. Thus the actual condition of valve 200 in FIG. 15 is typically more like what is shown in FIG. 29 (i.e., distal portion of valve (beyond sleeve 120) expanded radially out; proximal portion of valve (still within sleeve 120) still prevented by sleeve 120 from expanding radially out).

Figure 16:
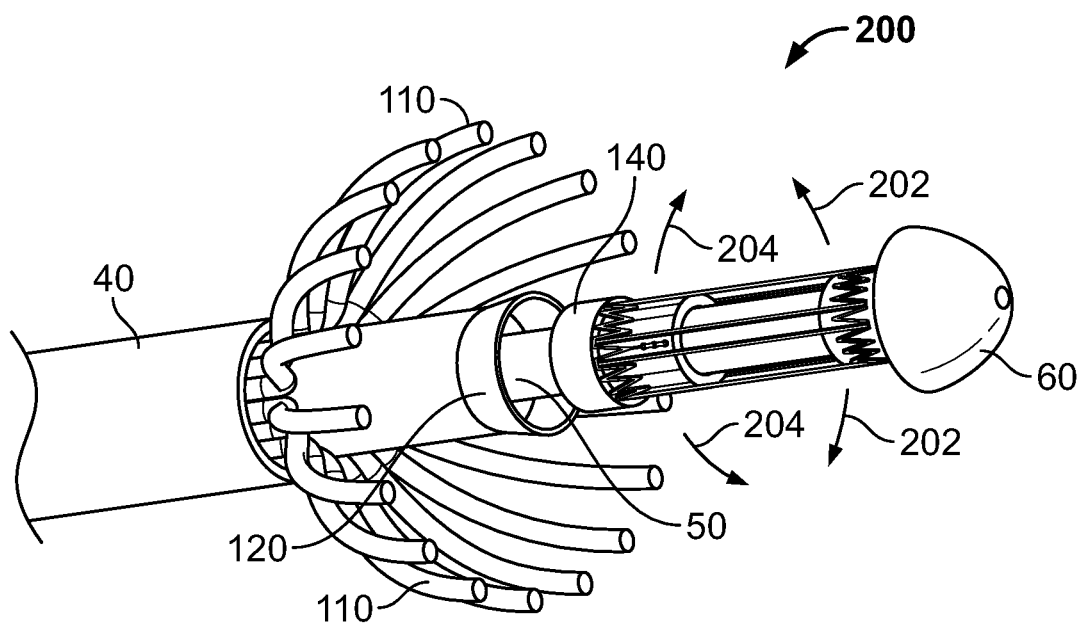
FIG. 16 is yet another view similar to FIG. 15 for a still later stage in operation of the apparatus in accordance with the invention.

FIG. 16 shows sleeve 120 pulled proximally back even farther so that valve 200 is now completely exposed. Once again, to avoid over-complicating the drawing, FIG. 16 omits the fact that at this stage heart valve 200 is typically expanded radially outwardly along its entire length as indicated by the arrows 202 and 204 in FIG. 16 and as is actually shown in FIG. 17. FIG. 16 does, however, serve to illustrate the point that prior to the deployment of valve 200 (i.e., prior to its radial outward expansion), the axial position of the collapsed valve is maintained in the apparatus by positioning the valve between distal tip 60 and a more proximal collar 140 on shaft 50.

Figure 17:
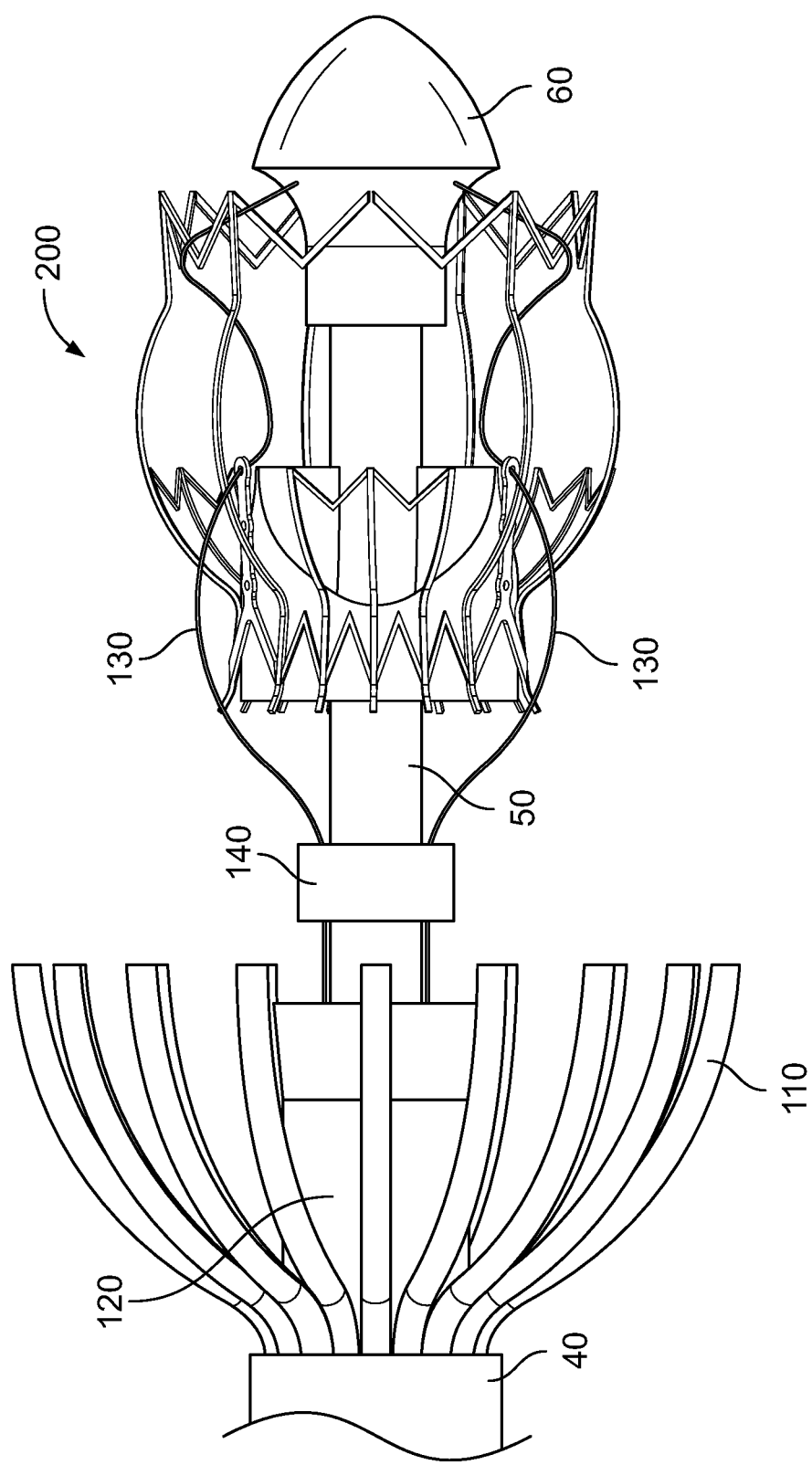
FIG. 17 is a simplified elevational view of an even later stage in operation of the FIG. 16 apparatus in accordance with the invention.
Figure 18:
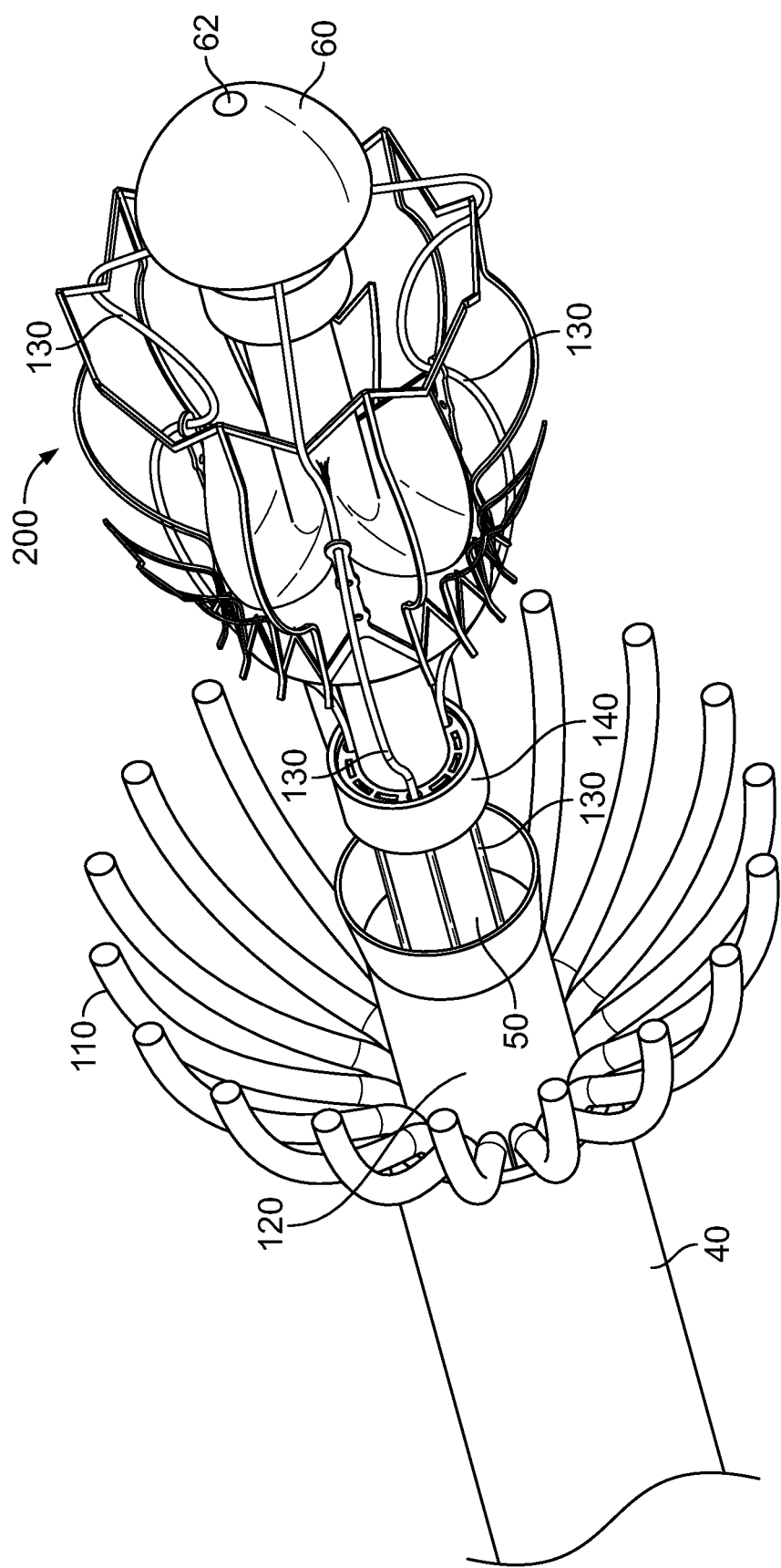
FIG. 18 is a simplified isometric or perspective view of what is shown in FIG. 17.

FIGS. 17 and 18 show additional structure that may be included in accordance with the invention. This is a system of flexible strands 130 that may be used (in conjunction with distal re-advancement of sleeve 120) to re-collapse valve 200 (either partly or wholly) in the event that it is found desirable or necessary to reposition the valve in the patient or to completely remove the valve from the patient after the valve has been partly or wholly expanded radially outwardly in the patient. FIGS. 17 and 18 show the routing of strands 130 in this embodiment. A typical strand 130 comes from a proximal portion of the apparatus between shaft 50 and sleeve 120. The strand 130 passes through an aperture in collar 140, and then runs along the outside of valve 200 to an aperture in distal tip 60. The strand passes through the interior of tip 60, and then through the central lumen of shaft 50, extending proximally all the way to the handle, where the strand ends can be controlled by the operator of the apparatus. There can be any number of similarly routed strands 130 spaced in the circumferential direction around the apparatus and valve 200. Strands 130 are shown in a relatively loose or relaxed condition in FIGS. 17 and 18. However, they can be tightened by pulling on their proximal portions.

Figure 19:
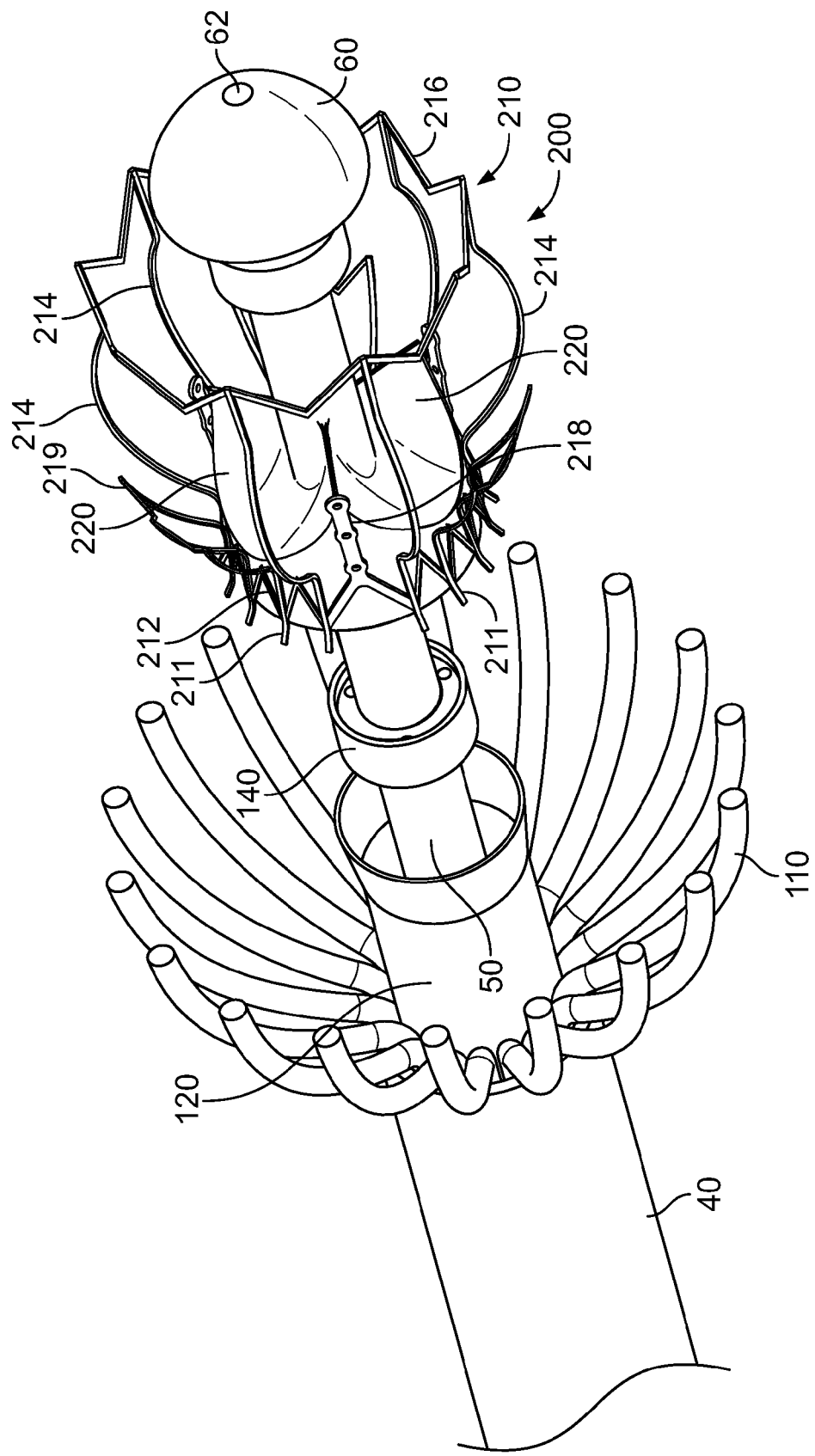
FIG. 19 is another view similar to FIG. 18 for a still later stage in operation of the apparatus in accordance with the invention.
Figure 20:
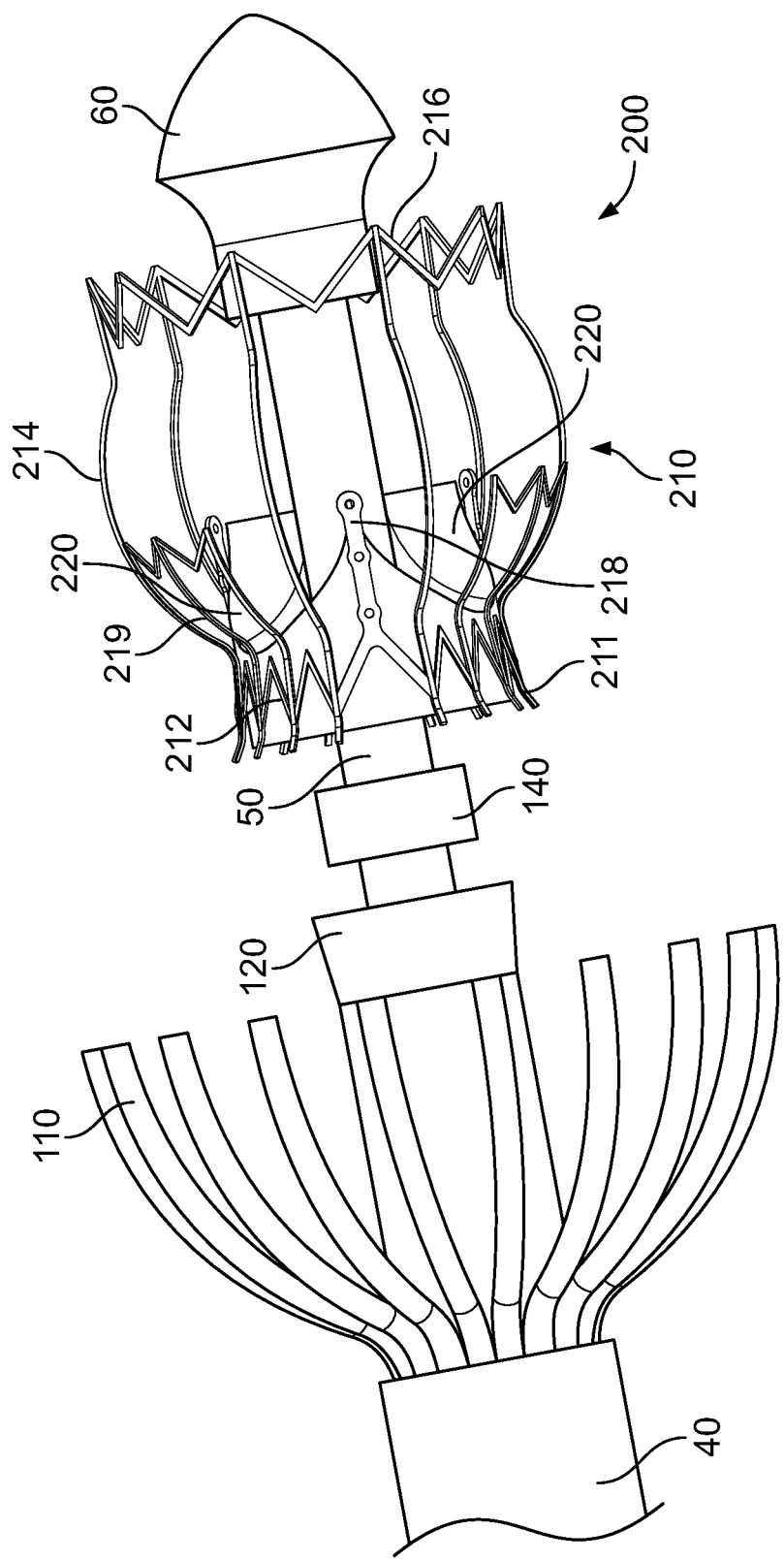
FIG. 20 is a simplified elevational view of what is shown in FIG. 19.

An example of how strands 130 may be used is as follows. The gradual proximal retraction of sleeve 120 (described in earlier paragraphs) allows heart valve 200 to gradually deploy radially outwardly. Strands 130 are relaxed or loose at this time. The gradual deployment of valve 200 may be observed by the operator of the apparatus (e.g., via x-ray, fluoroscopy, or the like). If the valve is not going in as desired, expansion of the valve can be stopped by stopping the proximal retraction of sleeve 120. Strands 130 can then be tightened by pulling proximally on their proximal portions, and at the same time sleeve 120 can be pushed in the distal direction. This combination of tightening strands 130 and pushing distally on sleeve 120 causes valve 200 to collapse back into the sleeve. The apparatus can then be repositioned to reposition valve 200 in the patient (after which the valve can be deployed again), or alternatively the valve can be completely removed from the patient with all of the surrounding instrumentation. Assuming that the valve remains in the patient, then when the operator of the apparatus is satisfied with its deployed position and condition, strands 130 can be removed (or effectively removed) by pulling on one proximal portion of each strand until the other end of that strand has been past valve 200 two times (once going in the distal direction, and then going in the proximal direction). FIGS. 19 and 20 show the condition of the apparatus after strands 130 have thus been removed (or effectively removed).

Strands 130 can be made of any suitably tensilely strong but laterally (transversely) flexible material. Examples include suture material, metal wire, or the like.

Because FIGS. 19 and 20 show valve 200 in the fully deployed condition and after strands 130 have been removed, these FIGS. offer the clearest views of valve 200 and therefore afford the best reference for the following further description of the valve. Although this description is provided in connection with FIGS. 19 and 20, it will be understood that the valve can be the same in all of the earlier-discussed FIGS. herein. On the other hand, it will also be understood that this particular construction of the prosthetic heart valve is only an example, and that many modifications, variations, and alternatives are also possible for the valve.

As was mentioned earlier in this specification, principal components of valve 200 include frame 210 (e.g., of a highly elastic metal such as nitinol) and a plurality of leaflets (e.g., three leaflets) 220 of a flexible material such as tissue that has been rendered effectively inert and otherwise made suitable for long-term, non-reactive use in a patient's body. Leaflets 220 are secured to frame 210 in such a way that the leaflets can open (to allow blood to flow through the valve from left to right as viewed in FIGS. 19 and 20) and close (to prevent blood from flowing through the valve from right to left as viewed in these FIGS.).

The illustrative configuration of valve 200 that is shown in the FIGS. herein is particularly adapted for use as a prosthetic aortic valve. Details of valve 200 will therefore be described in that context. It will be understood, however, that this is only an example, and that the prosthetic valve can be alternatively configured differently in some respects to adapt it for use as a replacement for other valves in the heart or circulatory system.

Frame 210 is preferably a continuous, one-piece, annular (ring-like) structure (e.g., a structure that has been cut (using a laser) from a tube and then further processed to achieve a desired shape). Frame 210 has a "lower" (upstream or blood inflow) portion 212 that extends in a serpentine (undulating or zig-zag) fashion all the way around the valve. This portion of frame 210 may be designed for implanting in or near the patient's native valve annulus. Frame 210 also includes an "upper" (downstream or blood outflow) portion 216 that also extends in a serpentine (undulating or zig-zag) fashion all the way around the valve. This portion of frame 210 may be designed for implanting in the patient's aorta downstream from the valsalva sinus of the patient. Frame portions 212 and 216 are connected to one another by a plurality of links or struts 214 that extend between those other frame portions at locations that are spaced from one another around the valve. Struts 214 may bow or bulge radially outwardly (as shown) to follow the inner surface of lobes of the valsalva sinus.

Frame 210 may include commissure post members 218 that extend up from lower portion 212 at appropriate locations around the valve (analogous to the commissures of the patient's native heart valve). These posts 218 can form important portions of the frame structure to which leaflets 220 are attached.

Frame 210 may also include other structures 219 that extend up and incline radially out from lower portion 212 to help hold back the patient's native valve leaflets, which (to the extent left remaining in the patient) are no longer functional.

Frame 210 may also include barbs (e.g., 211) at various locations to engage (and possibly penetrate) the patient's native tissue to help hold the valve in place where deployed in the patient.

The point of making annular frame portions 212 and 216 serpentine is to facilitate annular (circumferential, radial) collapse and subsequent re-expansion of the valve. Such collapse is preferably elastic, and the subsequent re-expansion is preferably resilient.

Although not shown herein, it will be understood that valve 200 may also include other components such as one or more layers of fabric and/or tissue on various parts of the valve. Such additional layers may be for such purposes as to promote tissue in-growth, to reduce the amount of contact between frame 210 and surrounding native tissue, to prevent moving portions of leaflets 220 from contacting frame 210, etc.

Figure 21:
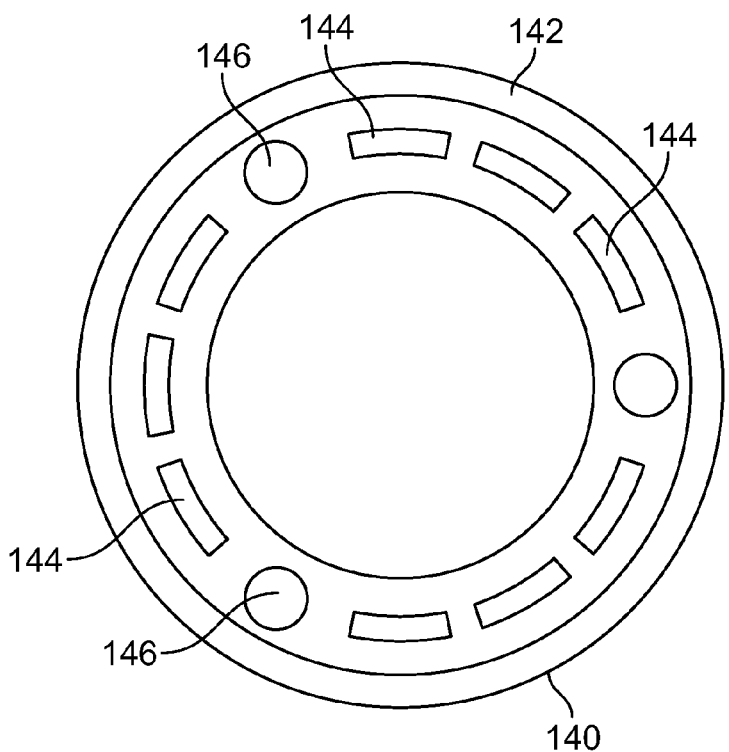
FIG. 21 is a simplified elevational view of an illustrative embodiment of one component from several earlier FIGS.
Figure 22:
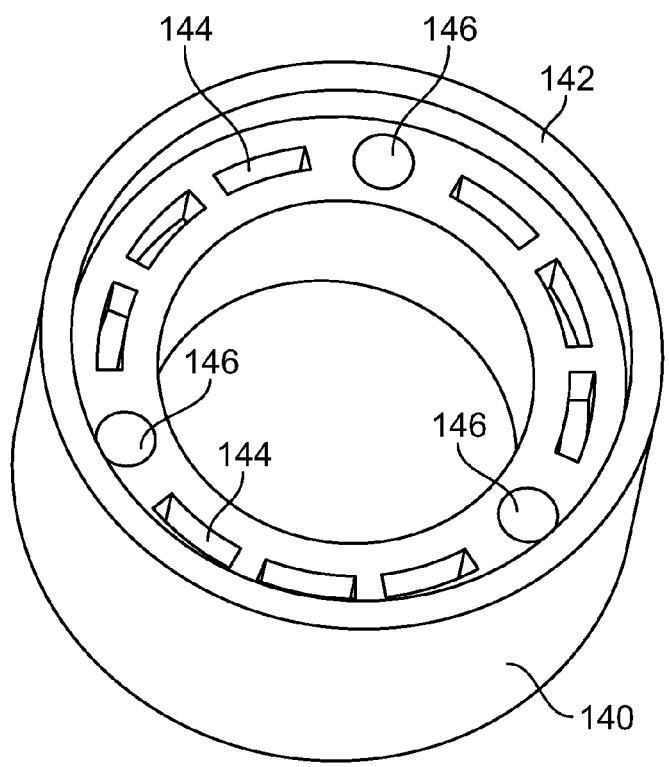
FIG. 22 is a simplified isometric or perspective view of what is shown in FIG. 21.

Illustrative details for collar 140 are shown in FIGS. 21 and 22. These features may include a distally extending, radially outer rim 142, within which a proximal portion of valve 200 can be received when the valve is in the collapsed condition. This structure 142 can help to keep valve 200 confined to its collapsed condition prior to deployment.

Other features of collar 140 may include recesses or sockets 144, into which extreme proximal portions (e.g., 211) of frame 210 may extend when valve 200 is in the collapsed condition. Such engagement between frame 210 and collar 140 can help ensure that valve 200 always maintains a known rotational (angular) orientation about the longitudinal axis of the apparatus. This can be helpful to ensure that rotation of apparatus 10 about its longitudinal axis produces exactly the same rotation of valve 200 about that axis. This may be important, for example, to help the operator of the apparatus position valve 200 for deployment with commissure posts 218 in a desired rotational or angular position relative to the patient's native valve commissures. As a specific example, it may be desirable for each commissure post 218 to be aligned with and inside a respective one of the patient's native valve commissures. This may necessitate rotation of apparatus 10 about its longitudinal axis, and features like 144 (with certain valve frame features received within those features 144) can help ensure that valve 200 has a known angular relationship to apparatus 10, and that this angular relationship is always maintained until the valve is deployed from the apparatus. Snug engagement between collar 140 and shaft 50 is also part of this aspect of the invention in this embodiment.

Still other possible features of collar 140 are apertures 146 for passage of above-described strands 130 through the collar.

FIGS. 23-26 illustrate another possible feature of the apparatus. This is an embolic protection structure 300, which may also include features for pushing back the leaflets of the native heart valve that is to be replaced by the prosthetic valve. Structure 300 will now be described.

A purpose of apparatus 300 is to capture any debris (e.g., emboli) that may be dislodged from inside the patient during deployment of prosthetic heart valve 200 and/or the expansion of fork fingers 110. Thus embolic protection apparatus 300 is typically deployed in the patient, early in the procedure, downstream from the location at which valve 200 will be deployed. For example, assuming that valve 200 is a replacement for the patient's native aortic valve, apparatus 300 may be deployed in the patient's aorta downstream from where the prosthetic valve will be employed. Apparatus 300 acts like a blood filter. It allows blood to flow through, but it captures any particles or the like that should not be allowed to remain in the patient's blood stream. After prosthetic valve 200 has been implanted, apparatus 300 is collapsed (still retaining any debris it has captured) and removed from the patient in the opposite way from which it was introduced.

In this embodiment, apparatus 300 is a structure somewhat like an umbrella. In particular, structure 300 has a central shaft 310, and a plurality of ribs or spokes 320 that are attached to a distal portion of shaft 310 and that can either collapse inwardly against (parallel to) shaft 310 or that can incline radially outwardly from shaft 310. Another element of structure 300 is a flexible, emboli-catching web or mesh (blood filter) 330 attached to ribs 320. Still other components of structure 300 are tethers 340 (shown only in FIG. 26 to avoid over-complicating the other FIGS.). Tethers 340 run inside the proximal portion of shaft 310 and come out of apertures in the side wall of shaft 310 at locations that are adjacent to ribs 320. Each tether 340 is attached to a respective one of ribs 320.

Before deploying valve 200, apparatus 300 may be introduced into the patient in a collapsed condition via proximal connector 70, a lumen through tube 100, and distal tip aperture 62. When apparatus 300 is at the desired location in the patient's circulatory system downstream from where valve 200 is to be implanted, the proximally directed tension on proximal portions of strands 340 may be released. This allows ribs 320 to resiliently deflect outwardly into an array somewhat like the ribs or spokes of an open umbrella. Ribs 320 carry out with them, and thus also open, blood filter web 330. These structures (i.e., 320 and 330) preferably bear against an annular portion of the inner surface of a blood vessel (e.g., the aorta) downstream from where valve 200 will be implanted in the patient.

After valve 200 has been deployed, embolic protection apparatus 300 may be collapsed again by pulling proximally on tethers 340. This causes ribs 320 to again become parallel to and against central shaft 310. Blood filter 330 (with any captured debris) is thereby also collapsed against central shaft 310. This allows apparatus 300 to be pulled back into device 10 via the aperture 62 in distal tip 60.

Note that apparatus 300 may include ribs 320 that extend proximally back from blood filter 330 per se. These rib extensions may serve the additional function of pushing back (radially outwardly) the leaflets of the patient's native heart valve prior to deployment of prosthetic valve 200.

Figure 23:
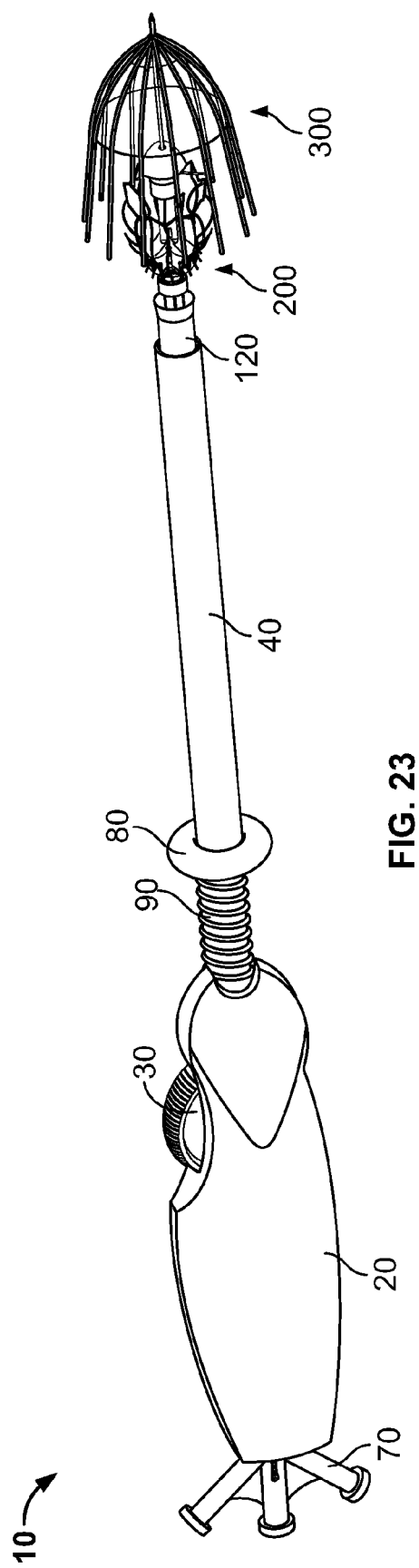
FIG. 23 is a view, similar in some respects to FIG. 4, showing illustrative embodiments of possible additional components in accordance with the invention.
Figure 24:
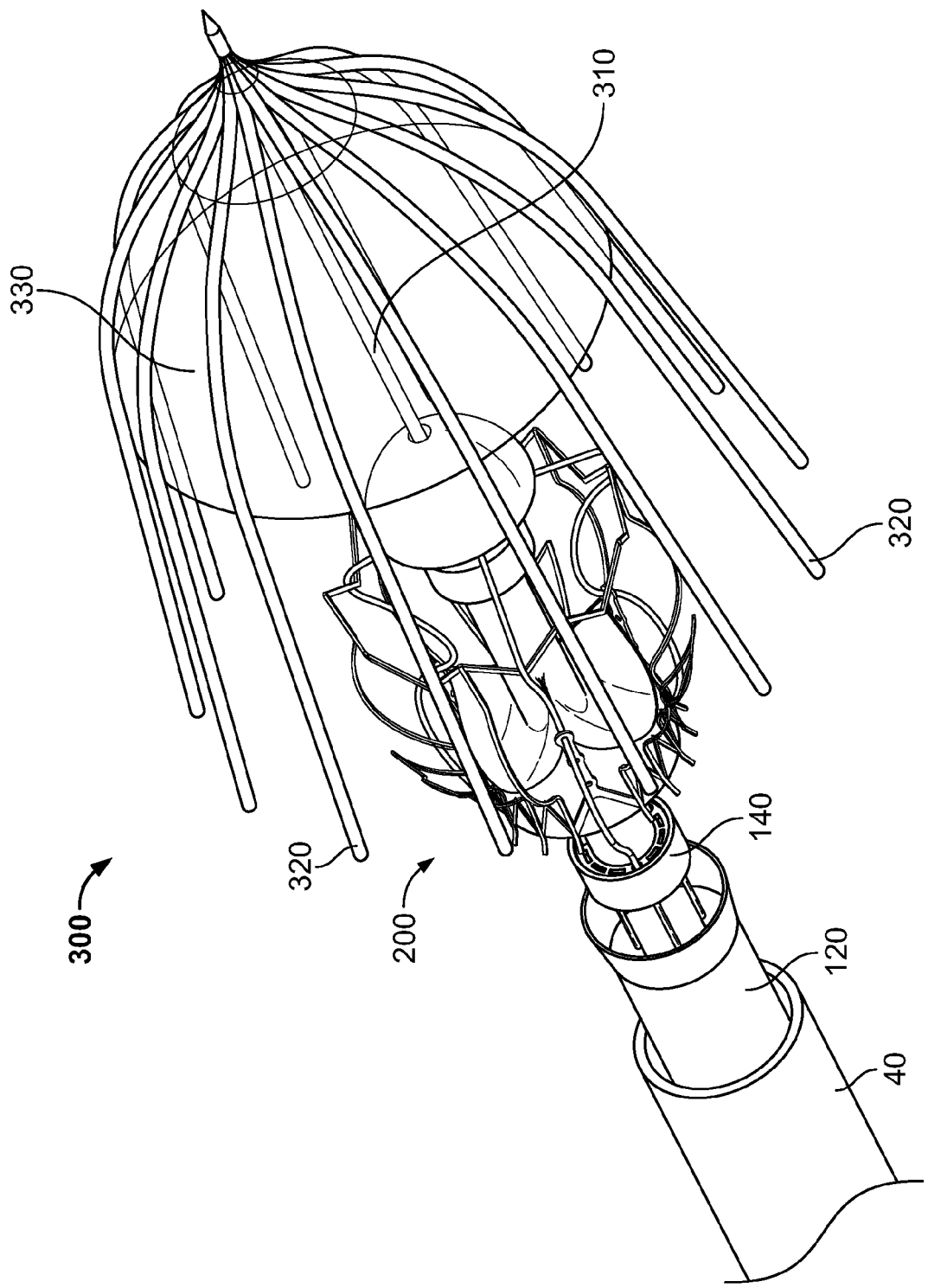
FIG. 24 is a simplified isometric or perspective view of portions of what is shown in FIG. 23.
Figure 25:
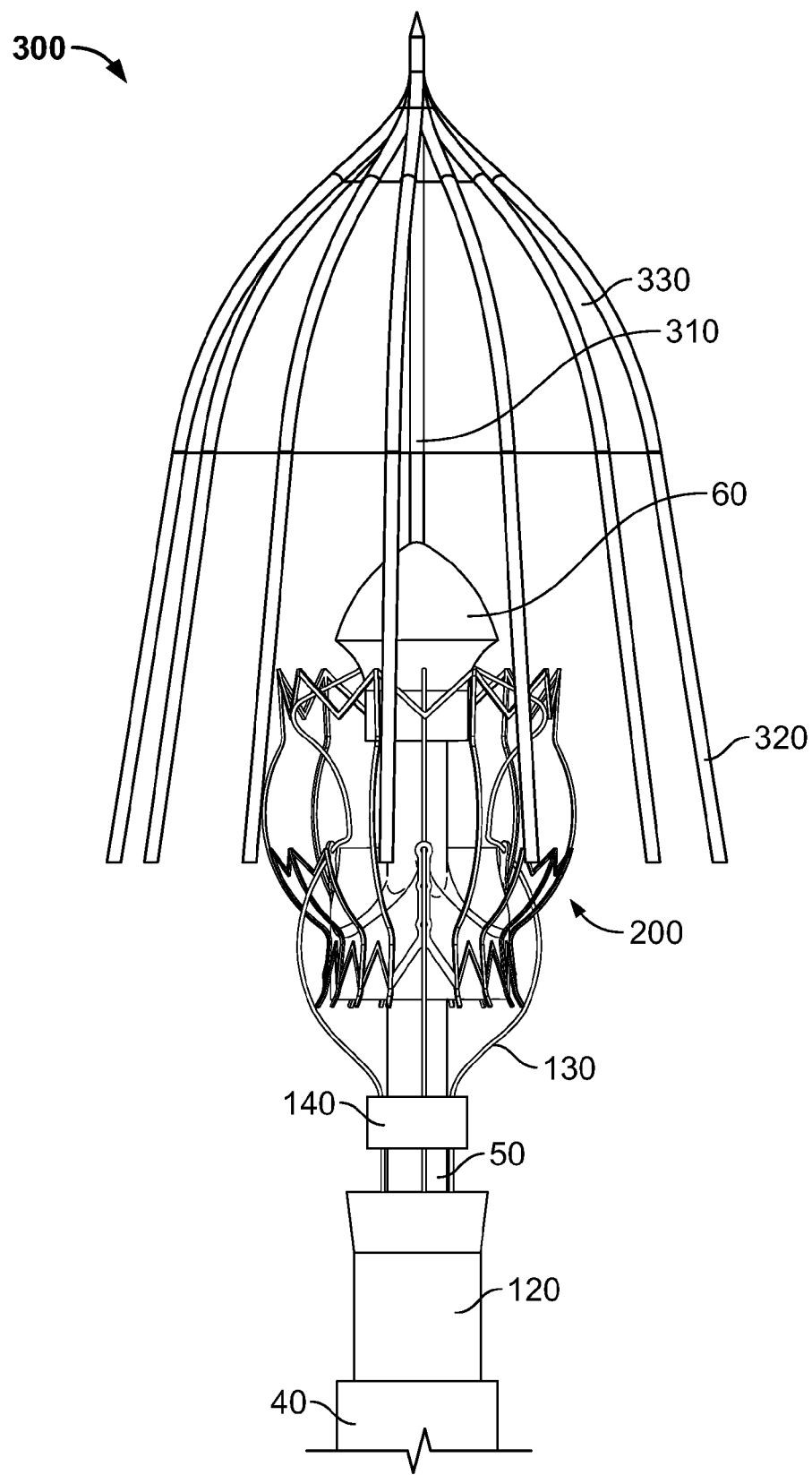
FIG. 25 is a simplified elevational view of what is shown in FIG. 24.
Figure 26:
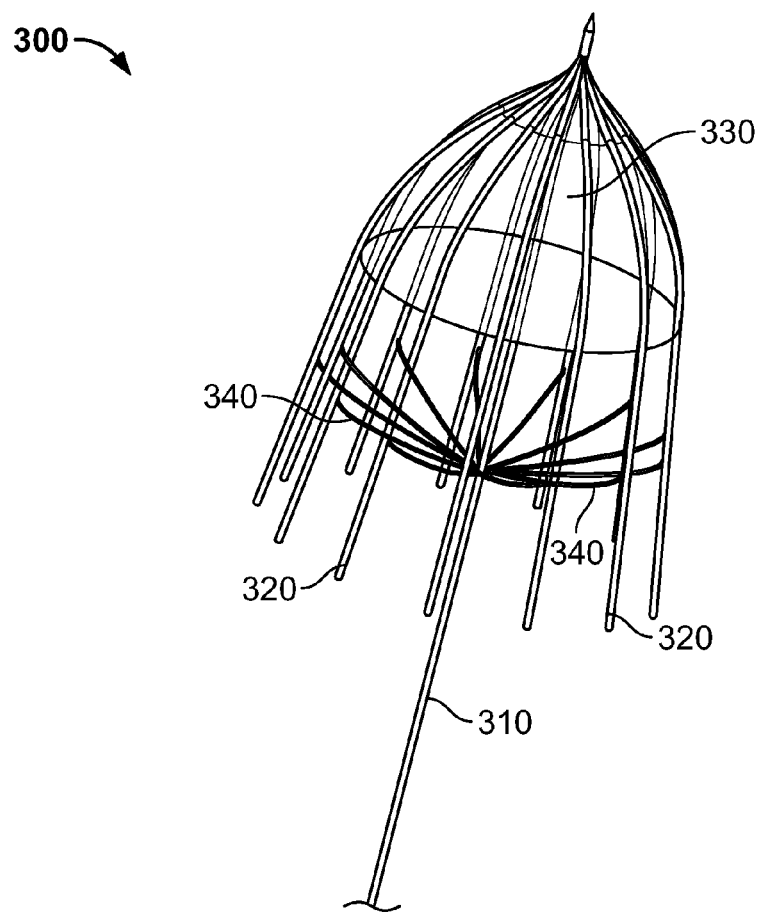
FIG. 26 is a simplified isometric or perspective view of portions of what is shown in FIGS. 23-25.

After apparatus 300 (with above-mentioned, optional, proximal, rib extensions) has been deployed, the distal portion of device 10 may be moved distally closer to apparatus 300. The distal portion of device 10 may then be opened and valve 200 may be deployed as shown in FIGS. 23-25. Because in this embodiment, deployed valve 200 may somewhat axially overlap with the proximal extensions of ribs 320, after deployment of valve 200, apparatus 300 may first be pushed in the distal direction to eliminate this overlap so that apparatus 300 can be re-closed without disturbing implanted valve 200. This is also a convenient point to mention that after valve 200 has been deployed (in any embodiment, with or without apparatus 300), shaft 40 may be pushed distally through the implanted valve to again close against distal tip 60. This restores the smooth outer surface to device 10, which facilitates proximal withdrawal of device 10 through the implanted valve without disturbing the valve. If apparatus 300 is employed, it is preferably collapsed and returned to the interior of device 10 (or completely removed via device 10) prior to full withdrawal of device 10 through the implanted valve.

Figure 27:
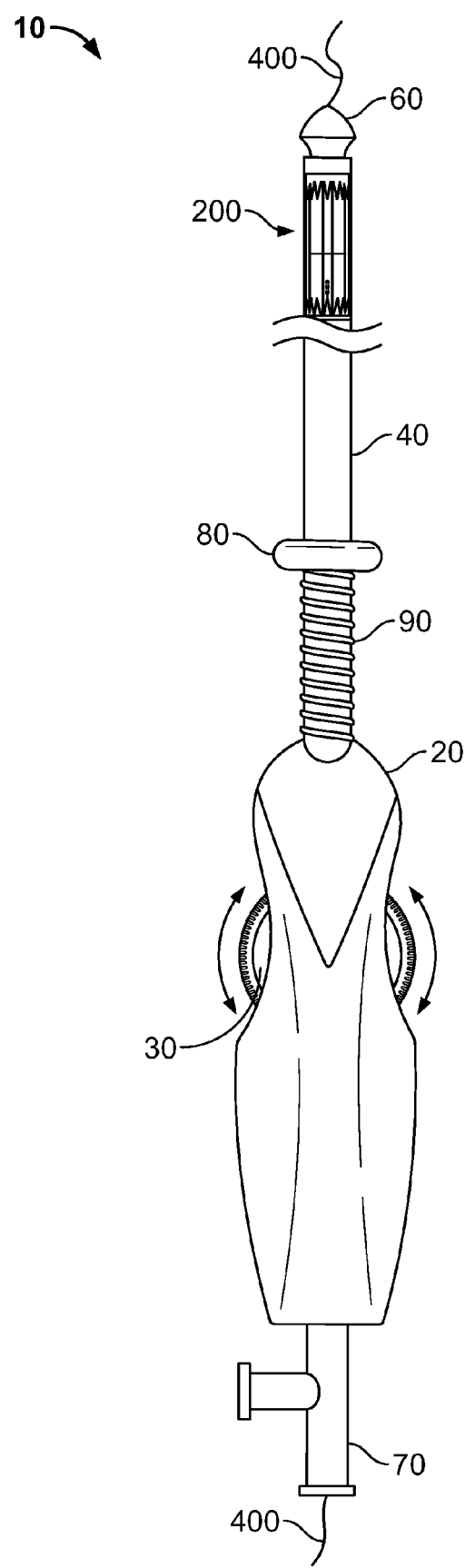
FIG. 27 is a simplified, partial, elevational view, partly in section, showing an illustrative embodiment of possible features in accordance with the invention.

FIG. 27 shows that a lumen through elements 70, 100, 60, 62 can be used for passage of a guide wire 400 through the apparatus. Thus a guide wire 400 can first be placed in the patient, and device 10 can thereafter be introduced into the patient by following along this guide wire. This guide wire lumen and/or other similar lumens through device 10 can alternatively or additionally be used for other purposes such as flushing, introduction and/or removal of other ancillary devices (e.g., embolic protection apparatus 300), etc.

Figure 28:
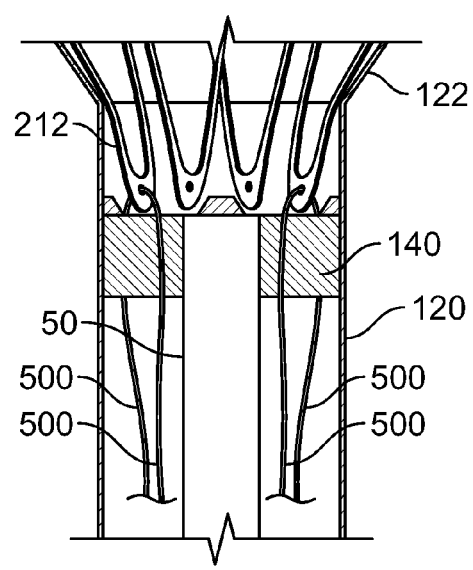
FIG. 28 is a simplified sectional view showing an illustrative embodiment of other possible features in accordance with the invention.

FIG. 28 shows other possible aspects of valve deployment and retrieval. FIG. 28 shows the upstream end of valve 200 inside sheath 120 and bearing on collar 140. Suture or wire strands 500 pass through collar 140 and are looped through upstream portions 212 of valve frame 210. Strands 500 can be pulled in the proximal direction to hold the proximal (upstream) end of valve 200 against collar 140. This also prevents the proximal end of valve 200 from expanding radially outwardly (even when sheath 120 is retracted proximally). However, when sheath 120 is retracted proximally past the proximal end of valve 200 and the tension on strands 500 is relaxed, the proximal end of valve 200 can expand resiliently outwardly. (FIG. 29 shows this structure again (although it omits depiction of strands 500 to avoid over-complicating the drawing) with the distal (downstream) portion of valve 200 released from sheath 120 and resiliently expanded outwardly, but with the proximal portion of the valve not yet released.)

FIGS. 28 and 29 show that the distal end of sheath 120 may flare radially outwardly as shown at 122. This feature and strands 500 can be used to re-collapse valve 200 prior to its final release from device 10 if for any reason it is desired to reposition the valve in the patient or remove the valve from the patient. A combination of pulling proximally on strands 500 and pushing sheath 120 distally can be used to collapse valve 200 back down into sheath 120 with the proximal end of the valve seated against collar 140. The valve can then either be positioned differently in the patient and again deployed, or the valve can be completely removed from the patient with device 10. Assuming that valve 200 is going to be implanted in the patient, when the operator of the apparatus is satisfied with the placement of the valve in the patient, the valve is finally released from device 10 by allowing the downstream end of the valve to deploy and anchor against the aortic wall, and then deploying the upstream valve end. Finally, strands 500 are removed by releasing one end of each strand loop and using the other end of that loop to pull the released end sufficiently far so that the strand no longer prevents release of the valve from device 10.

It will be understood that the foregoing is only illustrative of the principles of the invention and that various modifications can be made by those skilled in the art without departing from the scope and spirit of the invention. For example, the shapes and sizes of various components can be different from the shapes and sizes employed in the illustrative embodiments shown herein. As another example, the lateral stiffness of shaft 40 and/or other longitudinal elements within shaft 40 can be selected to render the apparatus suitable for different possible uses and/or preferences. Thus in some embodiments it may be desirable for the shaft portion of the apparatus to be relatively stiff or even rigid or substantially rigid (i.e., not flexible or bendable transverse to or laterally of its longitudinal axis). On the other hand, in other embodiments it may be desirable for the shaft portion of the apparatus (or certain parts of the shaft portion) to be more laterally flexible.

The invention claimed is:

1. Apparatus for delivering a prosthetic heart valve into a patient, comprising:
    a longitudinal outer shaft extending from a proximal portion of the apparatus to a distal portion of the apparatus, the outer shaft having a longitudinal axis and a fixed position relative to the proximal portion of the apparatus;
    a longitudinal inner shaft disposed inside the outer shaft, the inner shaft being longitudinally movable relative to the outer shaft;
    a tip structure mounted on a distal portion of the inner shaft for substantially closing a distal end of the outer shaft when the inner shaft is pulled proximally back relative to the outer shaft;
    a control wheel rotatable relative to the inner shaft and operable to move the inner shaft longitudinally relative to the outer shaft while the outer shaft remains in the fixed position, the control wheel having a circumference; and
    a prosthetic heart valve disposed around the inner shaft proximal of the tip structure and inside a distal portion of the outer shaft, the prosthetic valve being releasable from the apparatus when the tip structure is moved distally away from the distal end of the outer shaft and the prosthetic valve is shifted distally beyond the distal end of the outer shaft.

2. The apparatus as claimed in claim 1, further comprising a handle attached to a proximal portion of the outer shaft.

3. The apparatus as claimed in claim 2, wherein the control wheel is rotatably mounted within the handle so that a portion of the control wheel comprising less than the entire circumference of the control wheel protrudes from the handle.

4. The apparatus as claimed in claim 3, wherein the control wheel has an axis of rotation, the axis of rotation being disposed laterally of the longitudinal axis of the outer shaft.

5. The apparatus as claimed in claim 3, wherein the control wheel has an axis of rotation which intersects the longitudinal axis of the outer shaft.

6. The apparatus as claimed in claim 3, wherein the handle has a top side with a first aperture and the portion of the control wheel protrudes through the first aperture.

7. The apparatus as claimed in claim 6, wherein the handle has a bottom side with a second aperture, and the portion of the control wheel protrudes through the first aperture and the second aperture.

8. The apparatus as claimed in claim 1, wherein the inner shaft includes a rack extending along a length thereof, and the control wheel includes a spur gear engaged with the rack so that rotation of the control wheel causes longitudinal movement of the inner shaft relative to the outer shaft.

9. The apparatus as claimed in claim 8, wherein the spur gear remains in contact with the rack during the longitudinal movement of the inner shaft relative to the outer shaft at least until the prosthetic valve is shifted distally beyond the distal end of the outer shaft.

* * * * *